under 35 U.S.C. 154(b) by 279 days.

United States Patent
Bao

(10) Patent No.: US 11,478,517 B2
(45) Date of Patent: Oct. 25, 2022

(54) LIVE ATTENUATED RECOMBINANT HMPV WITH MUTATIONS IN PDZ MOTIFS OF M2-2 PROTEIN, VACCINE CONTAINING AND USE THEREOF

(71) Applicant: THE BOARD OF REGENTS OF THE UNIVERSITY OF TEXAS SYSTEM, Austin, TX (US)

(72) Inventor: Xiaoyong Bao, Galveston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 279 days.

(21) Appl. No.: 16/327,880

(22) PCT Filed: Aug. 22, 2017

(86) PCT No.: PCT/US2017/047998
§ 371 (c)(1),
(2) Date: Feb. 25, 2019

(87) PCT Pub. No.: WO2018/039221
PCT Pub. Date: Mar. 1, 2018

(65) Prior Publication Data
US 2019/0192592 A1 Jun. 27, 2019

Related U.S. Application Data

(60) Provisional application No. 62/378,371, filed on Aug. 23, 2016, provisional application No. 62/383,828, filed on Sep. 6, 2016.

(51) Int. Cl.
| | |
|---|---|
| *A61K 35/76* | (2015.01) |
| *C12N 7/00* | (2006.01) |
| *A61K 39/125* | (2006.01) |
| *A61K 39/145* | (2006.01) |
| *A61K 39/15* | (2006.01) |
| *A61K 39/285* | (2006.01) |
| *A61K 39/12* | (2006.01) |
| *A61P 31/14* | (2006.01) |
| *A61K 39/00* | (2006.01) |

(52) U.S. Cl.
CPC ............ *A61K 35/76* (2013.01); *A61K 39/12* (2013.01); *A61K 39/125* (2013.01); *A61K 39/145* (2013.01); *A61K 39/15* (2013.01); *A61K 39/285* (2013.01); *A61P 31/14* (2018.01); *C12N 7/00* (2013.01); *A61K 2039/5254* (2013.01); *A61K 2039/5258* (2013.01); *A61K 2039/543* (2013.01); *C12N 2760/18322* (2013.01); *C12N 2760/18334* (2013.01)

(58) Field of Classification Search
None
See application file for complete search history.

(56) References Cited

U.S. PATENT DOCUMENTS

2003/0232061 A1* 12/2003 Fouchier .......... G01N 33/56983
435/235.1

FOREIGN PATENT DOCUMENTS

EP    WO 2009/062532    *    5/2009    ........... A61K 39/155

OTHER PUBLICATIONS

Ren et al. (Journal of Virology, vol. 499, p. 361-3682012).*
Ren et al. PLOS, 2014, vol. 9, p. 1-9.*
Bao et al., PLOS, 2013, vol. 8, p. 1-9.*
Chen et al. (Virology, 2016, p. 361-368).*

* cited by examiner

*Primary Examiner* — Agnieszka Boesen

(57) ABSTRACT

The present application generally relates to the development of live attenuated Pneumoviridae strains suitable for use as a vaccine. Particularly, human metapneumovirus (hMPV) ΔM2-2 strains (rhMPV-E30M31 and rhMPV-E40L42D44) containing point mutations in a PDZ motif of M2-2, which results in a strain that is both attenuated and immunogenic and, notably, maintains the function of F and G proteins. These live attenuated hMPV strains should be suitable for use in a vaccine capable of providing protection against respiratory infection elicited by hMPV. Additionally, human respiratory syncytial virus (hRSV) strains containing point mutations in a PDZ motif of M2-2 should also be suitable for use as a vaccine capable of providing protection against respiratory infection elicited by hRSV. These Pneumoviridae strains should be useful in vaccines for use in humans and animals, e.g., companion animals and livestock, in treating or providing immunoprotection against respiratory infections.

20 Claims, 31 Drawing Sheets

Specification includes a Sequence Listing.

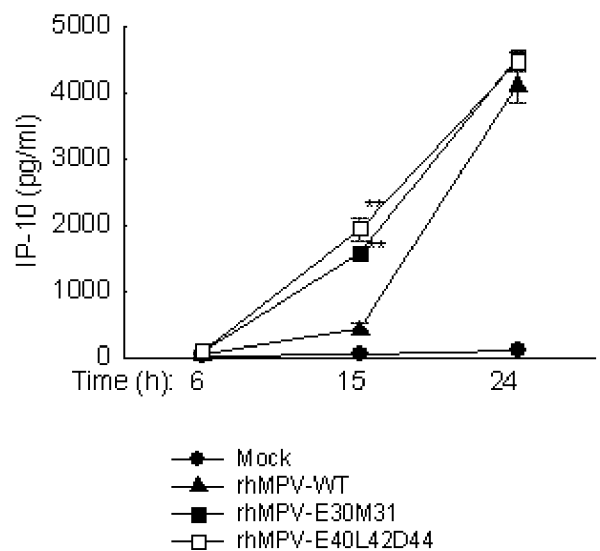
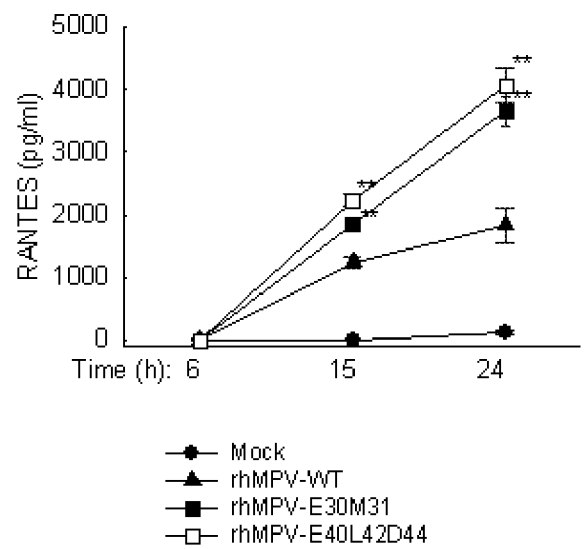

Day 14
- Base line
- rhMPV-WT
- rhMPV-E30M31
- rhMPV-E40L42D44

FIG 11B

Day 21
- Base line
- rhMPV-WT
- rhMPV-E30M31
- rhMPV-E40L42D44

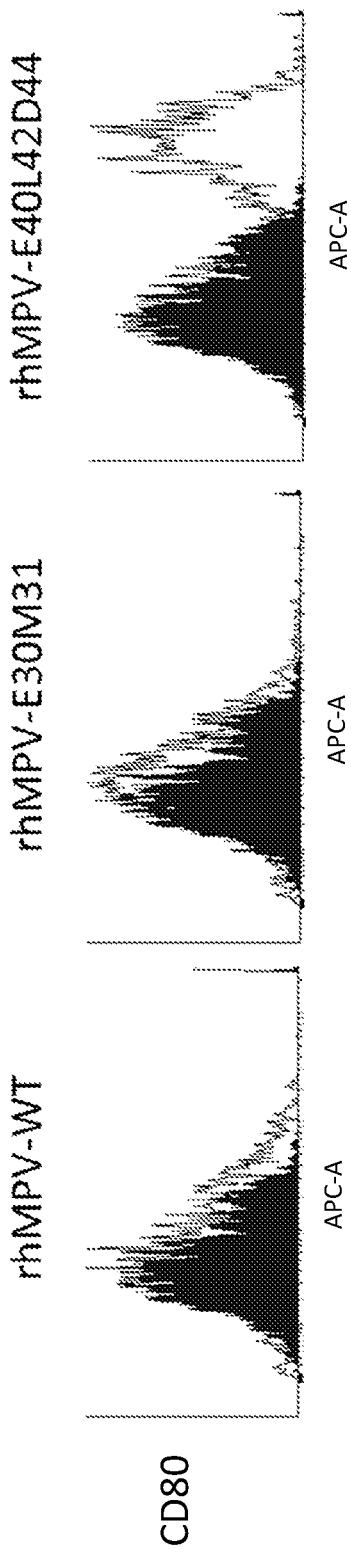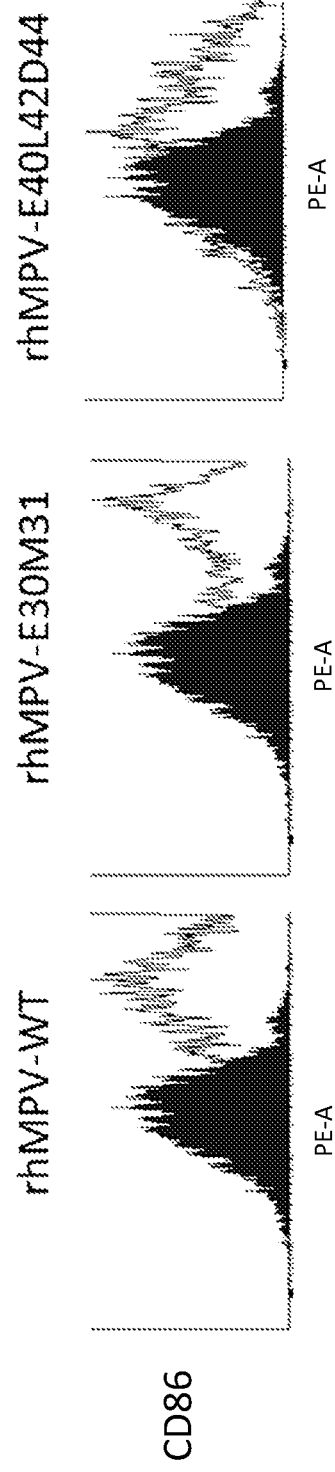
FIG 13A
FIG 13B

LIVE ATTENUATED RECOMBINANT HMPV WITH MUTATIONS IN PDZ MOTIFS OF M2-2 PROTEIN, VACCINE CONTAINING AND USE THEREOF

PRIORITY APPLICATIONS

This application is a 371(c) National Phase of International Appl. No. PCT/US2017/047998, filed Aug. 22, 2017, which claims priority to U.S. Provisional Appl. No. 62/383,828, filed Sep. 6, 2016, and U.S. Provisional Appl. No. 62/378,371, filed Aug. 23, 2016, the disclosures of each of which are hereby incorporated by reference in their entireties.

SEQUENCE LISTING

This application includes as part of its disclosure a biological sequence listing which is being concurrently submitted through EFS-Web. Said biological sequence listing is contained in a file named "49561o1602.txt" which was created Feb. 12, 2019, and has a size of 3,908 bytes, and is hereby incorporated by reference in its entirety.

FEDERAL FUNDING

The invention was funded by American Lung Association grant RG232529N; American Heart Association grant 12BGIA12060008; and NIAID grant 1R01AI107033-01.

FIELD OF THE INVENTION

The invention generally relates to the development of a live attenuated Pneumoviridae strain and vaccine compositions containing the strain. These strains and vaccines containing may be used in humans and animals, e.g., companion animals (such as horses, cats and dogs) and livestock (such as cows, turkeys, chicken, and sheep), for treating or providing immunoprotection against respiratory infections elicited by species of the Pneumoviridae family, in particular human metapneumovirus (hMPV) and human respiratory syncytial virus (hRSV), which are the causative agents of lower and upper respiratory infections.

BACKGROUND OF THE INVENTION

Human metapneumovirus (hMPV) is a leading cause of lower respiratory tract disease in children, the elderly, and immunocompromised patients worldwide[1-3]. Symptoms commonly associated with hMPV include cough, fever, nasal congestion, and shortness of breath. It induces clinical syndromes ranging from mild disease to more severe disease, with high fever, wheezing, severe cough, difficulty in breathing, tachypnea, bronchiolitis and pneumonia.

hMPV is the first and only identified human pathogen belonging to the genus *Metapneumovirus* in the Paramyxoviridae family (which has since been dissolved and the Pneumoviridae family was created in its place). hMPV is a negative single-stranded RNA virus.

hMPV was first isolated in the Netherlands in 2001 from respiratory specimens of young children suffering with acute respiratory tract illness and represents a major respiratory pathogen worldwide. Epidemiological studies show that hMPV is responsible for 5% to 15% of pediatric hospitalizations for respiratory tract infections.

Phylogenetic analysis of hMPV has demonstrated the existence of two main genetic lineages (subtype A and B) containing within them the subgroups A1/A2 and B1/B2, respectively. hMPV is genetically similar to the avian pneumoviruses type A and B and, in particular, type C.

hMPV is an enveloped, negative sense single-stranded RNA virus whose genome size is approximately 13,000 nucleotides but varies depending on the strain. Examples of the subgroup A indicate that the strain CAN97-83 is 13,335 nucleotides and NL/00/1 is 13,350 nucleotides, and for the subgroup B: CAN98-75 is 13,280 nucleotides and NL/1/99 is 13,293 nucleotides.

The hMPV genome includes eight genes encoding nine proteins: nucleocapsid (N), phosphoprotein (P), matrix (M), second matrix (M2-1, M2-2), fusion (F), small hydrophobic (SH), attachment (G) and RNA-dependent RNA polymerase (L). The gene order in hMPV is represented as 3'-N-P-M-F-M2-SH-G-L-5'. The G protein is a transmembrane surface glycoprotein, which initiates the virus-host cell membrane attachment and so considered as a key player in viral replication. The F protein is required for the fusion of virus with host cell membrane and is capable of being accessed by neutralizing antibodies. The nucleocapsid (N), phosphoprotein (P) and RNA-dependent RNA polymerase (L) proteins along with M2 protein are involved in RNA synthesis.

The genomic organization of hMPV is analogous to human respiratory syncytial virus (hRSV); however, hMPV lacks the hRSV non-structural genes, NS1 and NS2, and the open reading frames of hMPV are organized differently than those of hRSV, i.e., 3'-NS1-NS2-N-P-M-SH-G-F-M2(1+2)-L-5'.

Like hMPV, hRSV is also a negative single-stranded RNA virus of the Pneumoviridae family that causes respiratory tract infections. hRSV is a major cause of lower respiratory tract infections and hospital visits during infancy and childhood. In the United States, 60% of infants are infected during their first RSV season and nearly all children will have been infected with the virus by 2-3 years of age. Individuals who suffered severe RSV infection during the first few months of life are at an increased risk of recurrent wheezing and asthma. For some children, RSV can cause bronchiolitis, leading to severe respiratory illness requiring hospitalization, and may cause death in patients that are immunocompromised or premature infants.

Natural infection with RSV induces protective immunity which wanes over time, possibly more so than other respiratory viral infections, and thus people can be infected with RSV multiple times. Sometimes an infant can become symptomatically infected more than once, even within a single RSV season. Severe RSV infections have increasingly been found among elderly patients. Young adults can be re-infected every five to seven years, with symptoms similar to a sinus infection or a cold.

Compared with RSV, infection with hMPV tends to occur in slightly older children and to produce disease that is less severe. However, co-infection with both viruses can occur, and is generally associated with worse disease.

To date, treatment for both hMPV and hRSV has been limited to, at most, supportive measures, e.g., fluids and oxygen until the illness runs its course.

Previous attempts to develop vaccines to these viruses have been unsuccessful. Indeed, an RSV vaccine trial in 1960s using an inactivated virus failed to protect vaccinated children and, moreover, increased disease severity in children who had been vaccinated. Although there is much active investigation into the development of a vaccine, at present no such vaccine exists and, thus, a need remains to develop effective therapeutic approaches against infection by Pneumoviridae family members, such as hRSV and hMPV.

SUMMARY OF THE INVENTION

The present invention relates to novel Pneumoviridae, in particular hMPV and hRSV, vaccine strains that display reduced virulence while maintaining immunogenicity and protective properties and immunologic compositions comprising these strains and the use thereof.

In one embodiment, the invention provides a live attenuated Pneumoviridae strain containing a mutation in a PDZ-binding motif of M2-2 that disrupts M2-2-mediated immune evasion, wherein the live attenuated strain elicits immunoprotection against the virus.

The function and/or expression of F protein and/or G protein may be maintained in the mutated strain.

The live attenuated strain may be a human metapneumovirus (hMPV), human respiratory syncytial virus (hRSV), a bovine respiratory syncytial virus (BRSV), an ovine respiratory syncytial virus (ORSV), or an avian metapneumovirus (AMPV). In a preferred embodiment, the strain is hMPV or hRSV.

In one aspect, the live attenuated strain contains a mutation in a single PDZ-binding motif of M2-2. The mutations may comprise multiple-site mutagenesis, e.g., 2 point mutations or 3 point mutations within the PDZ-binding motif.

In another aspect, the PDZ motif that is mutated is the PDZ-binding motif having the amino acid sequence of 29-DEMI-32 (SEQ ID NO:16) or the amino acid sequence of 39-KEALSDGI-46 (SEQ ID NO:17).

In another aspect, the live attenuated strain is rhMPV-E30M31 or rhMPV-E40L42D44 or the progeny of either strain.

In yet another aspect, the live attenuated strain displays (i) reduced M2-2-mediated suppression of immune gene expression in response to infection as compared to a wild-type strain; (ii) reduced M2-2-mediated enhancement of viral genome replication in response to infection as compared to a wild-type strain; and/or (iii) reduced M2-2-mediated inhibition of MAVS signaling as compared to a wild-type strain.

The invention also provides a live attenuated human metapneumovirus (hMPV) strain comprising a variant of rhMPV-E30M31 or rhMPV-E40L42D44. The function and/or expression of F protein and/or G protein may be maintained in the variant.

The invention further contemplates an immunogenic composition comprising a live attenuated Pneumoviridae strain according to any of the foregoing claims further comprising at least one pharmaceutically acceptable carrier or excipient and/or an immune adjuvant. The immunogenic composition may be suitable for topical, parenteral, or enteral administration.

The invention also encompasses a method of eliciting an immune response, e.g., a Th1 and/or Th2 response, in a subject in need thereof by administering a composition comprising a prophylactically or therapeutically effective amount of a live attenuated Pneumoviridae strain, e.g., hMPV or hRSV, or an immunogenic composition according to any of the foregoing claims. The subject may also be administered palivizumab or another monoclonal antibody specific to the RSV fusion (F) protein.

The immune response may be characterized by one or more of enhanced IRF-3 nuclear translocation; enhanced p65 nuclear translocation; increased chemokine gene expression; increased cytokine gene expression; and increased dendritic cell and/or T cell migration and maturation. Additionally, the immune response may be characterized by an increase in one or more of IL-1α, IL-1β, IL-6, IL-12, IFN-β, IFN-γ, G-CSF, GM-CSF, TNF-α, KC, MCP-1, MIP-1α, MIP-1β, and RANTES.

The method can be used to treat or prevent human metapneumovirus (hMPV) or human respiratory syncytial virus (hRSV) infection in a human, e.g., an infant, a child, or an elderly person and/or is immunocompromised, or a non-human subject, e.g., an equine, a canine, a feline, a bovine, an ovine, or an avian subject.

Also contemplated by the invention is a method of treating or preventing Pneumoviridae infection, e.g., infection with hMPV and/or hRSV, in a subject by administering a therapeutically or prophylactically effective amount of a live attenuated Pneumoviridae strain or immunogenic composition according to any of the foregoing claims. The subject may also be administered palivizumab or another monoclonal antibody specific to the RSV fusion (F) protein.

DESCRIPTION OF THE FIGURES

Figures 1C, 1D:
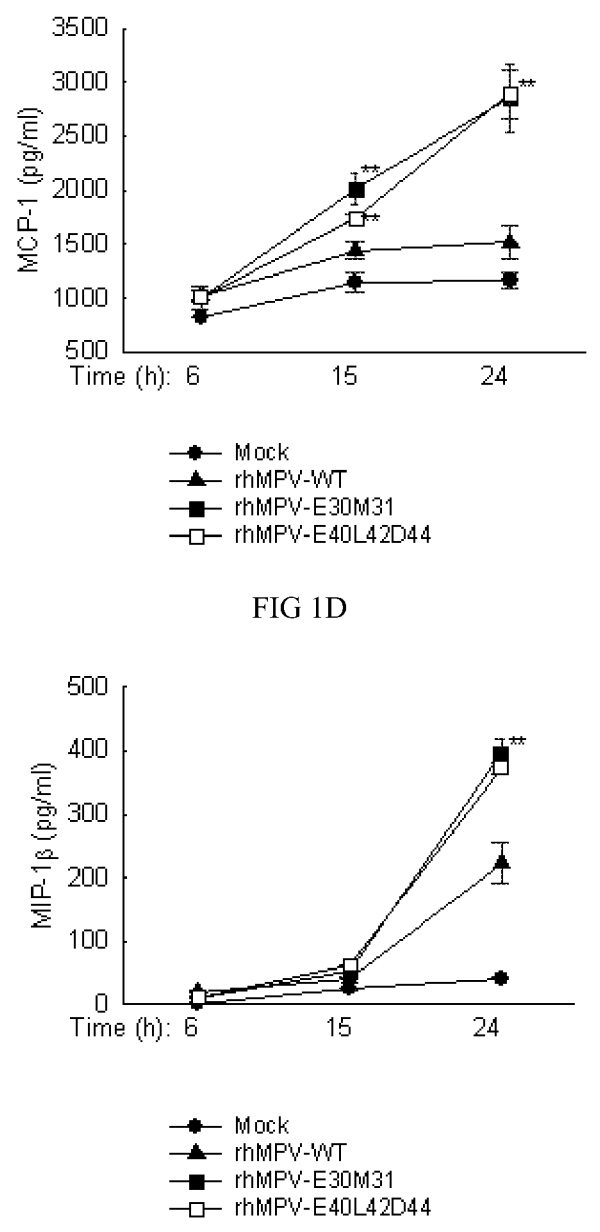

FIG. 1A-G contain data demonstrating that PDZ motifs 29-DEMI-32 and 39-KEALSDGI-46 are important for hMPV-induced innate immune response, in particular, immune mediator induction by rhMPV mutants. A549 cells in triplicate were mock infected or infected with rhMPV-WT, rhMPV-E30M31, or rhMPV-E40L42D44, at MOI of 2, for various times as indicated. The secretion of various cytokines and chemokines in cell supernatants was measured by Bio-plex and/or ELISA for the following chemokines/cytokines: IL-8 (Panel A), IL-6 (Panel B), MCP-1 (Panel C), MIP-1β (Panel D), IP-10 (Panel E), RANTES (Panel F), and IFN-β (Panel G). Data shown are from three independent experiments and are expressed as mean±SE. *: $P<0.05$, and **: $P<0.01$, relative to rhMPV-WT-infected A549 cells.

Figures 9G, 9H:
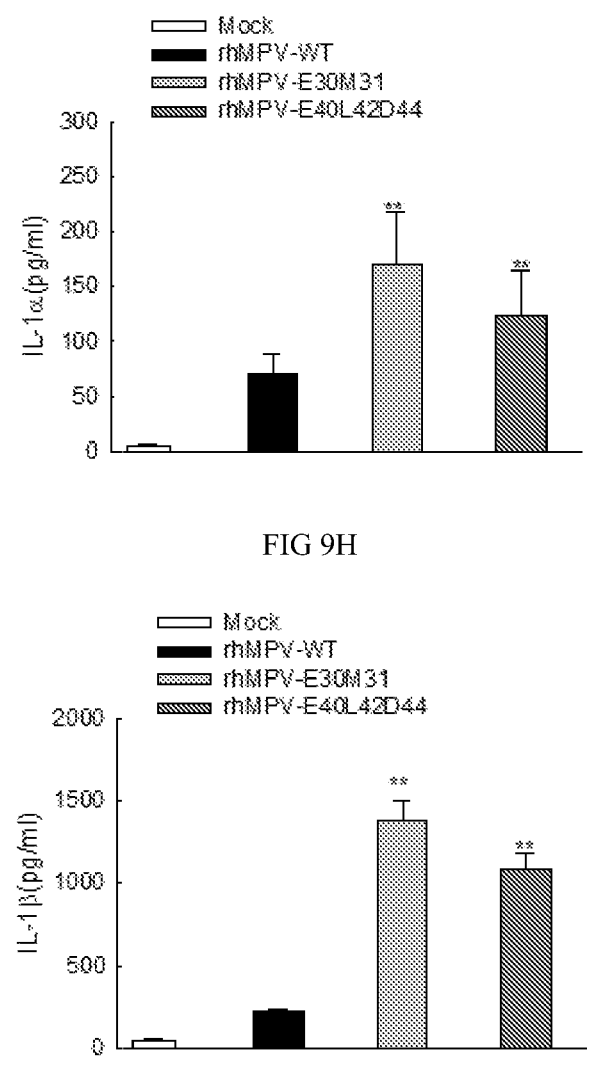
Figures 9K, 9L:
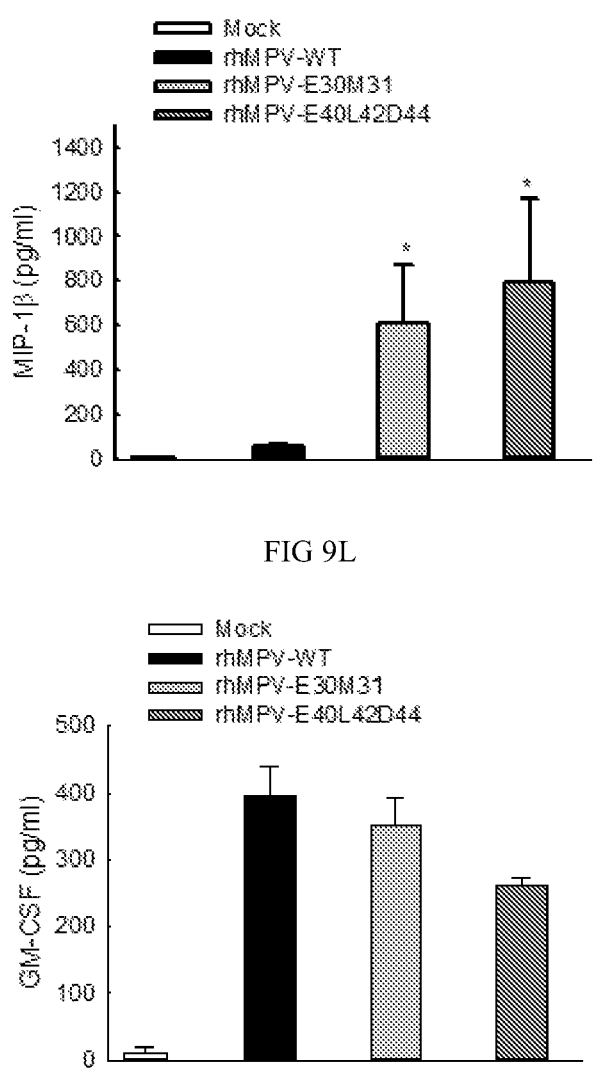

FIG. 9A-L contain data demonstrating the effect of M2-2 PDZ motifs on pulmonary cytokine and chemokine production in hMPV-infected lung. Bronchoalveolar lavage samples were collected from mock-, rhMPV-WT-, and rhMPV-mutant-infected BALB/c mice ($5\times10^6$ pfu/mice), at day 1 post infection and were assessed for IFN-β by ELISA (Panel F). Other cytokine and chemokine production was measured by a multi-Plex Cytokine detection system for: IL-6 (Panel A), MCP-1 (Panel B), KC (Panel C), TFN-α (Panel D), RANTES (Panel E), IL-1α (Panel G), IL-1β (3 (Panel H), G-CSF (Panel I), MIP-1α (Panel J), MIP-1β (Panel K), and GM-CSF (Panel L). Data are mean±SEM from n=10-12 mice in each group from three independent experiments. *: P<0.05 and **: P<0.01 for comparison with mutant-infected samples from rhMPV-WT-infected mice.

Figures 10A, 10B:
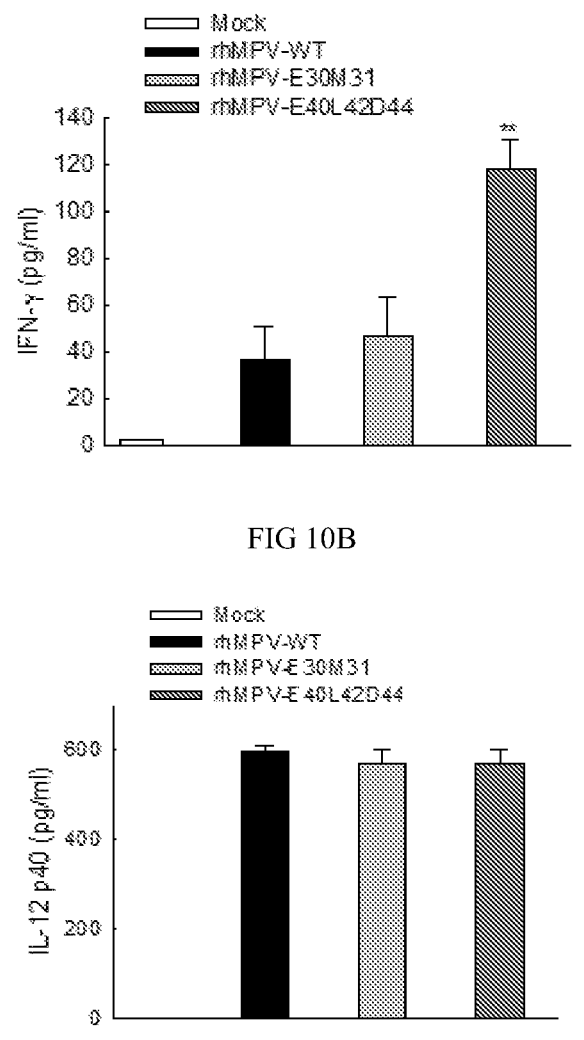
Figures 10C, 10D:
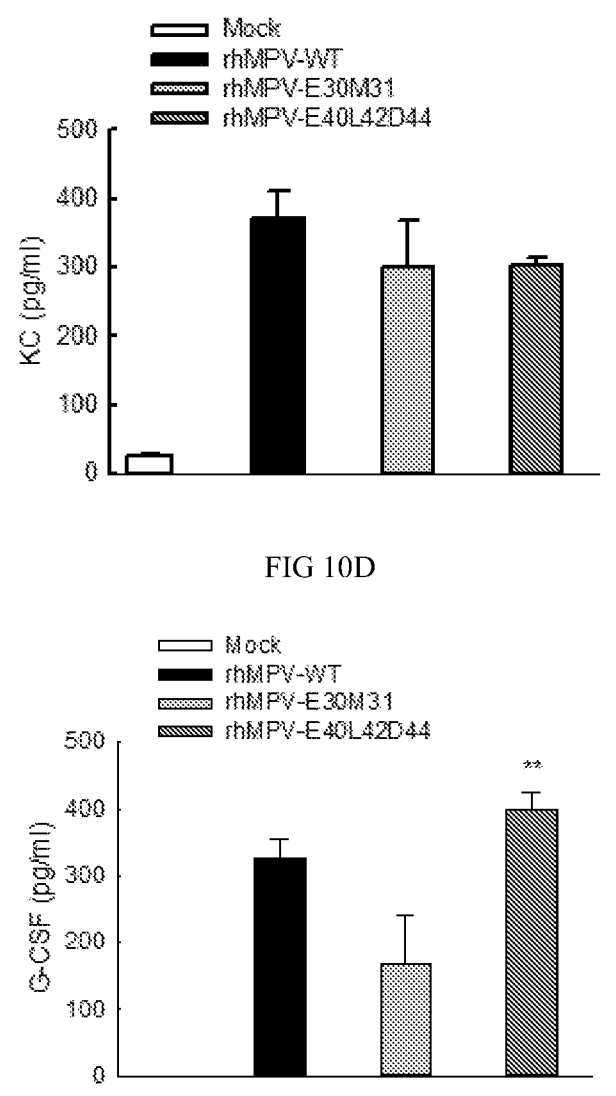
Figures 10E, 10F:
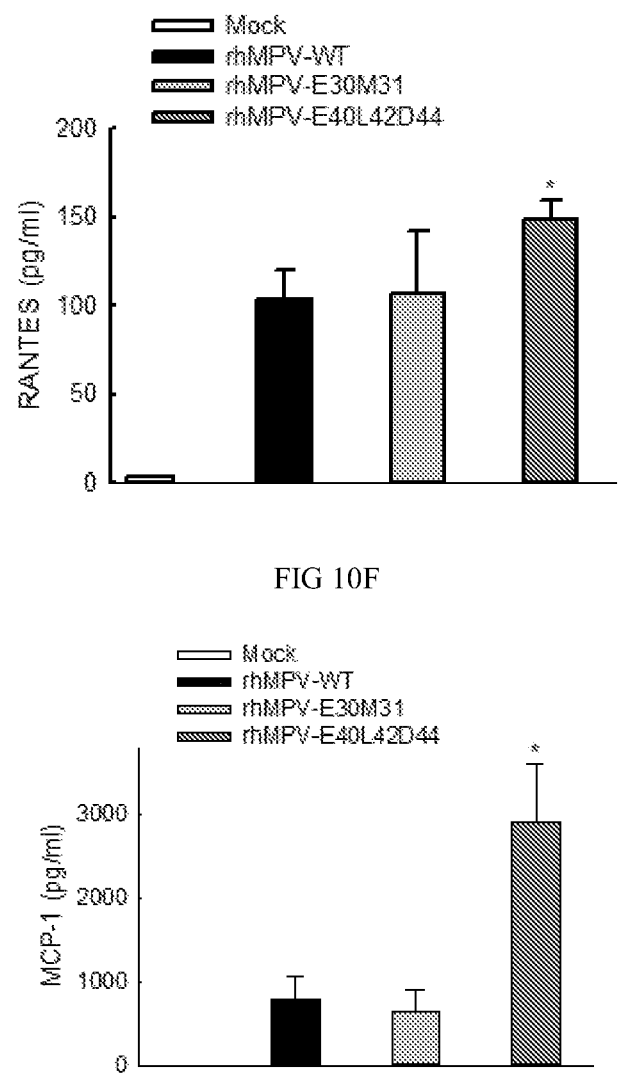

FIG. 10A-F contain data demonstrating the effect of M2-2 PDZ motifs on pulmonary cytokine and chemokine production in hMPV-infected lung. The cytokines and chemokines assayed were: IFN-γ (Panel A), IL-12 p40 (Panel B), KC (Panel C), G-CSF (Panel D), RANTES (Panel E), and MCP-1 (Panel F). The experiments were done as for FIG. 9A-L, except that the bronchoalveolar lavage samples were collected at day 5 post infection. Data are mean±SEM from n=10-12 mice in each group from three independent experiments. *: P<0.05 and **: P<0.01 for comparison with mutant-infected samples from rhMPV-WT-infected mice.

Figure 11C:
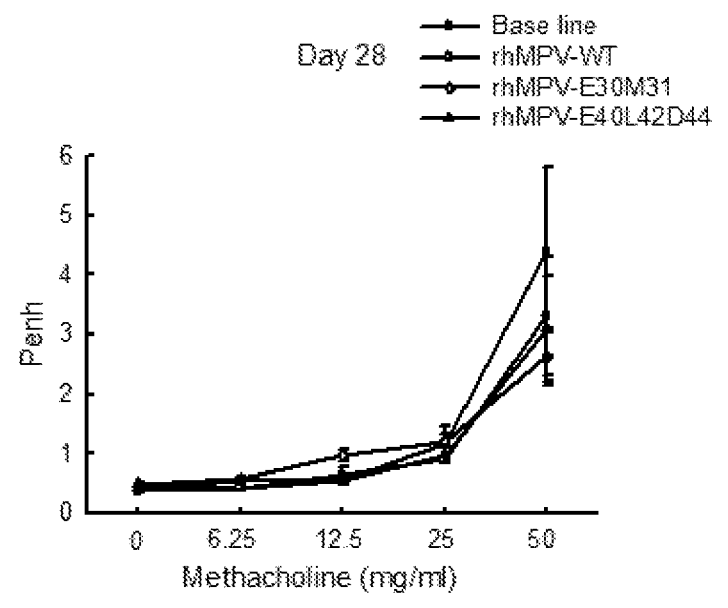

FIG. 11A-C contain data reporting on lung function in hMPV-infected mice. Mice were infected with hMPV ($5\times10^6$ pfu/mice), and baseline and post-methacholine challenge Penh values were determined by unrestrained plethysmography (Buxco) for a period of 28 days. Penh is a dimensionless value that represents a function of the ratio of peak expiratory flow to peak inspiratory flow and a function of the timing of expiration. Penh following methacholine challenge at day 14 (Panel A), 21 (Panel B) and 28 (Panel C) post infection. No significance respiratory damages were seen by mutants.

Figures 12A, 12B:
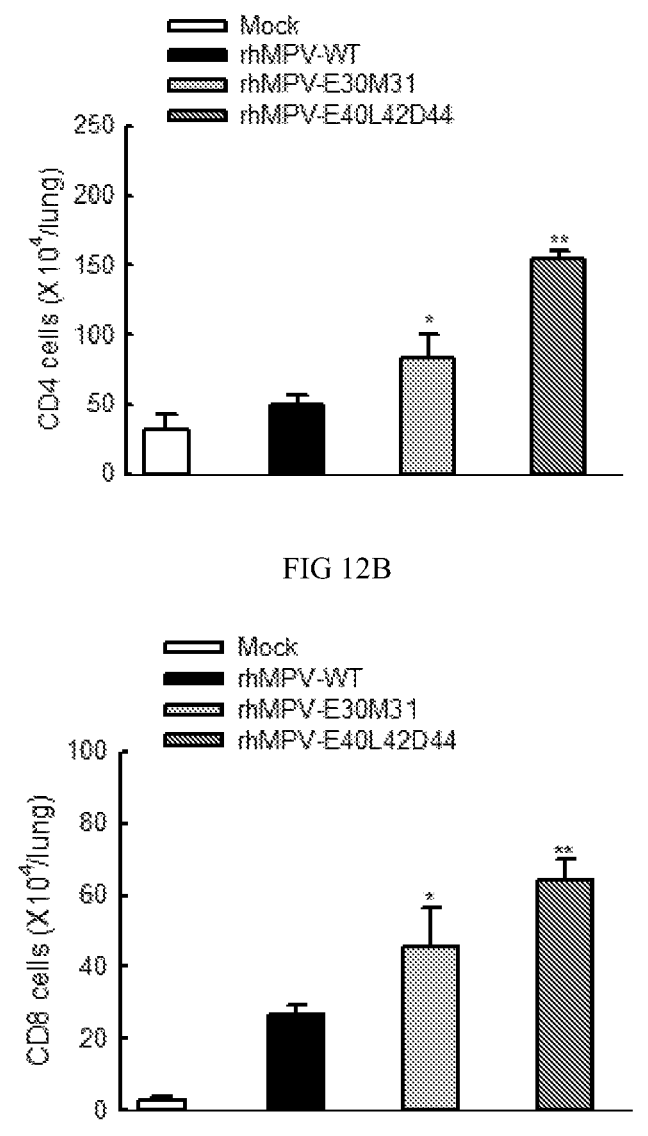
Figures 12C, 12D:
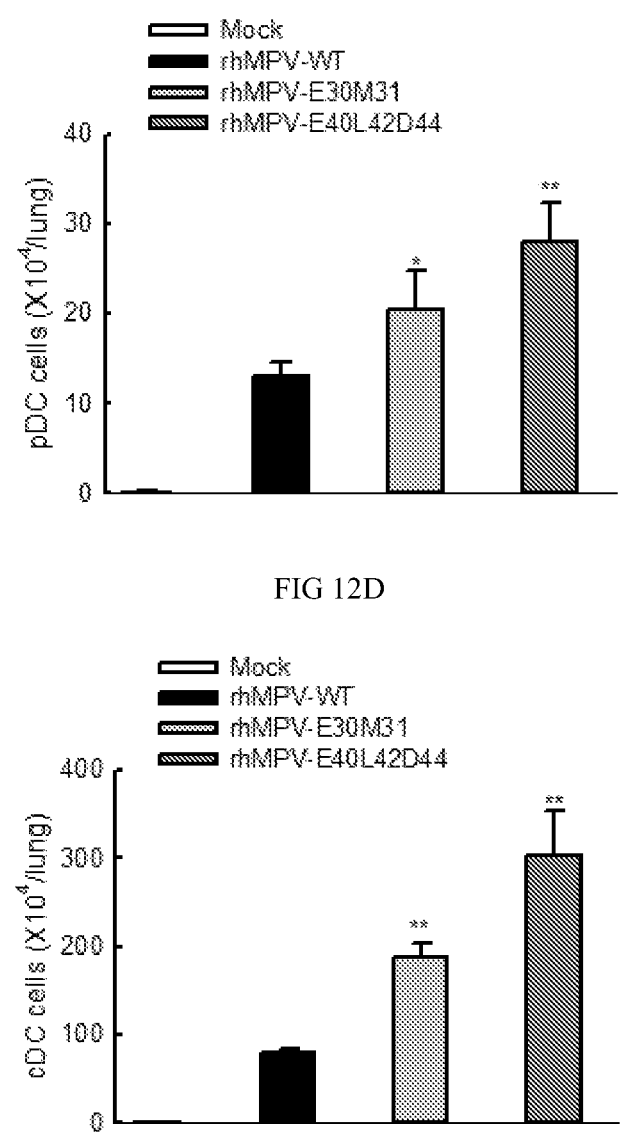

FIG. 12A-D contain data demonstrating the effect of M2-2 motifs on dendritic cell (DC) and T cell migration and maturation. Mice were infected with rhMPV or mock infected. At day 7 p.i., pulmonary CD4 T cells (Panel A), CD8 T cells (Panel B), pDC (Panel C) and cDC (Panel D) were quantified by FACS. The total cell numbers are presented as means±SEM, n=4 in each group from two independent experiments.

Figures 13C, 13D:
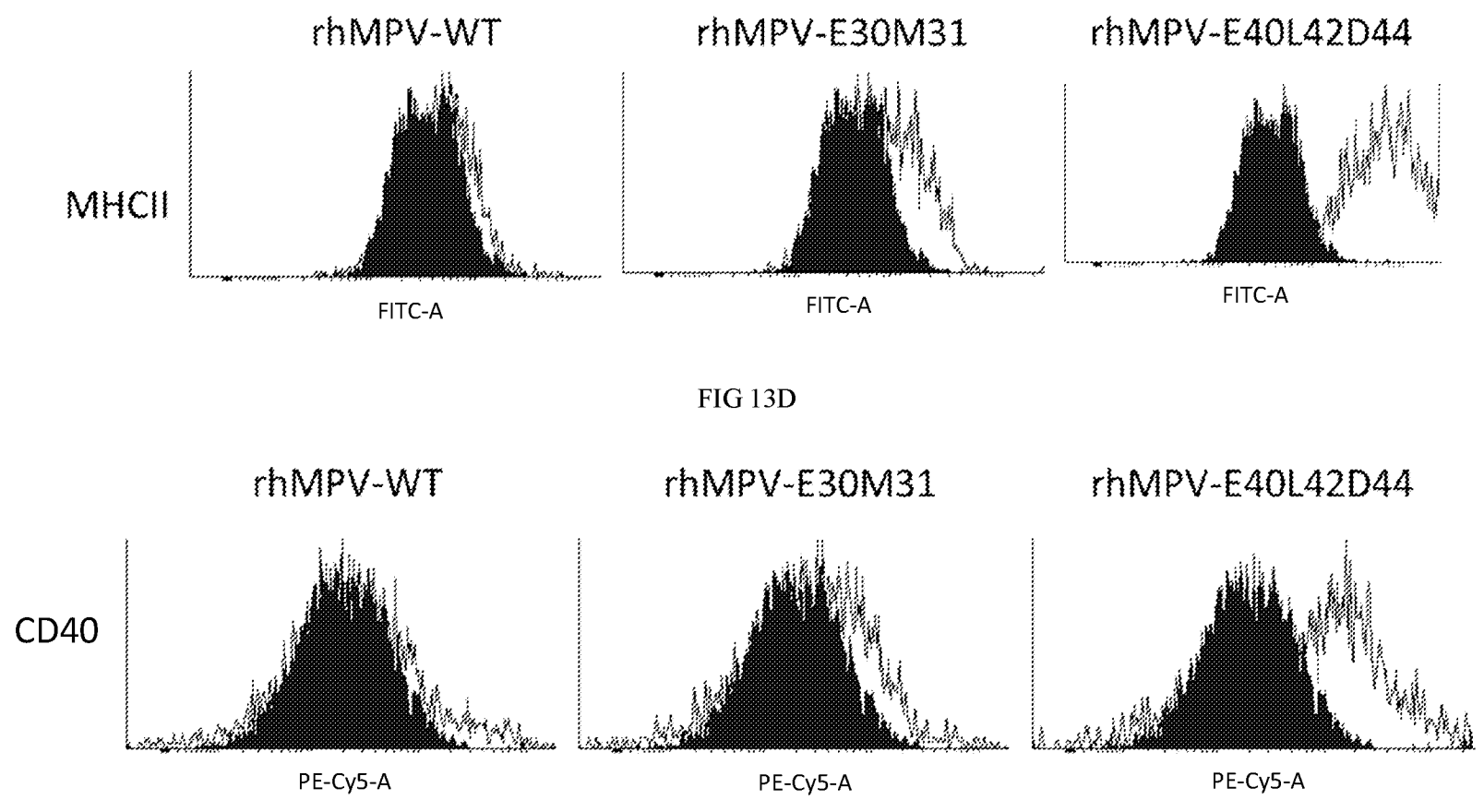

FIG. 13A-D contain data demonstrating the effect of M2-2 motifs on dendritic cell (DC) maturation by comparing the expression of CD80 (Panel A), CD86 (Panel B), MEW II (Panel C) and CD40 (Panel D) on the cell surface of lung CD11C+ cells from WT and mutant-infected mice. Representative histograms to elucidate the expression of DC maturation are shown.

Figure 14:
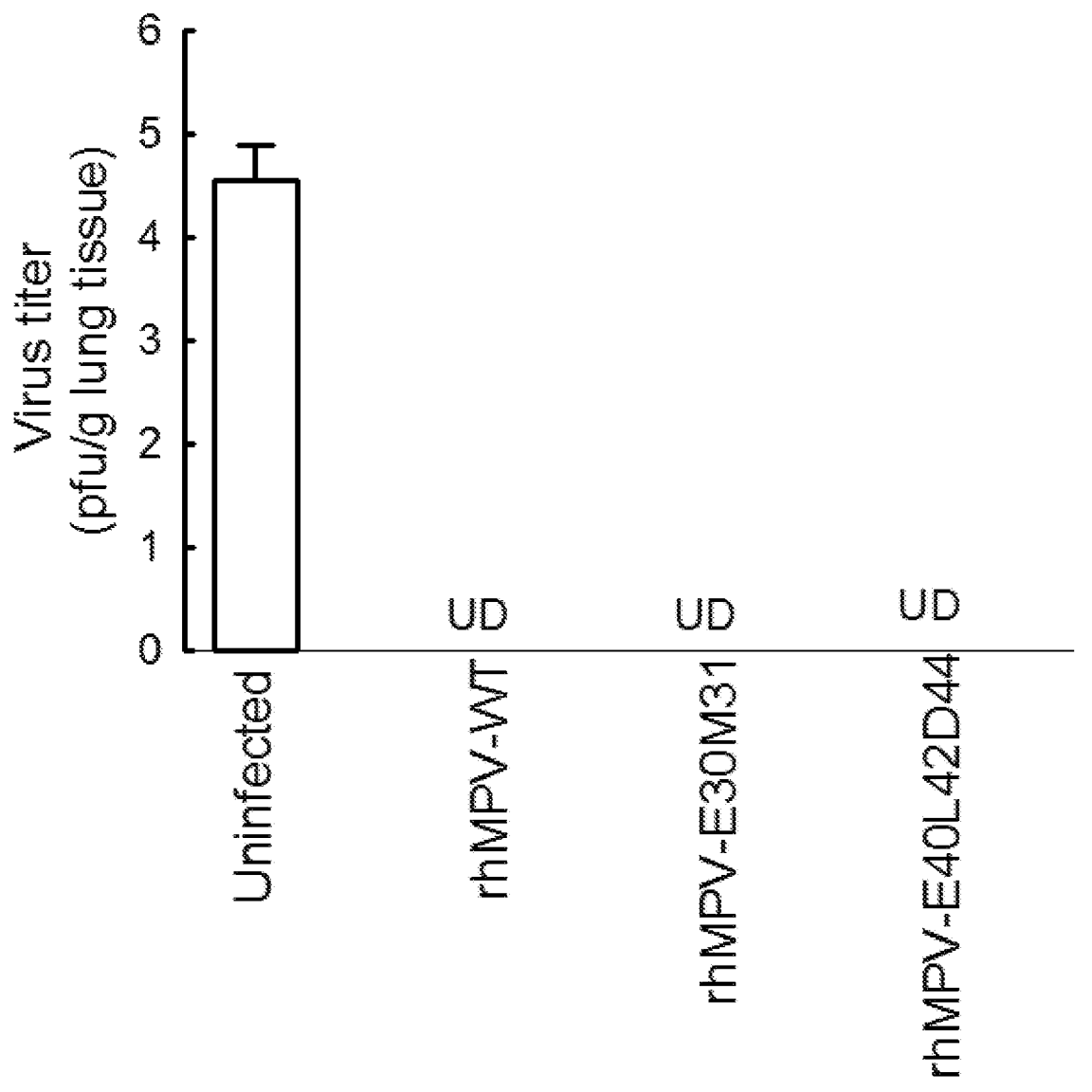

FIG. 14 contains data demonstrating that mutant viruses launch comparable immune protection. Mice were infected with viruses as described in previous figures. Uninfected mice were used as controls. After 28 days, the mice were challenged by hMPV and lungs were harvested at day 5 post challenging to detect the infectious particles.

DETAILED DESCRIPTION OF THE INVENTION

Figure 1A:
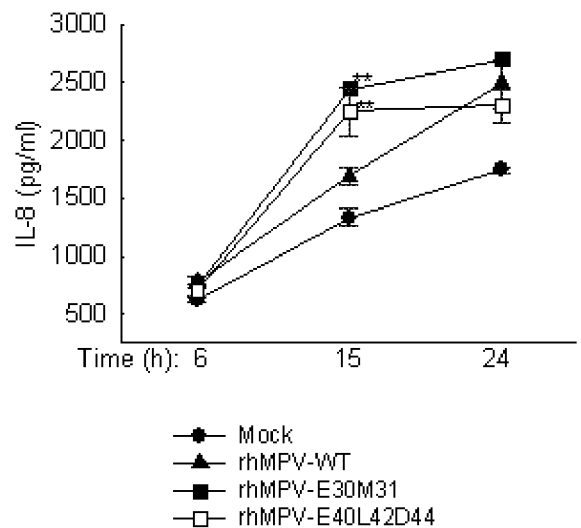
Figure 1B:
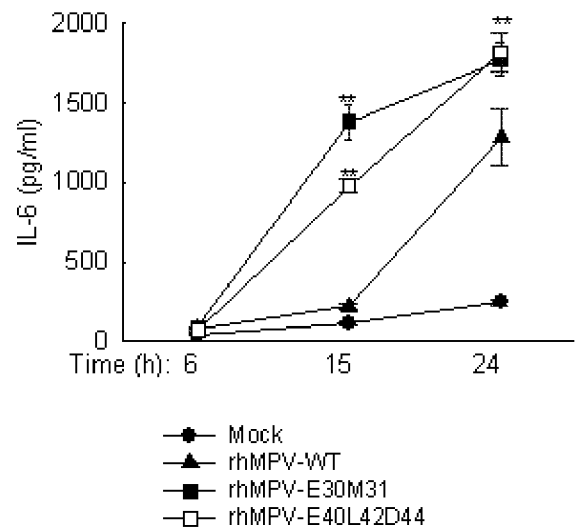
Figure 1G:
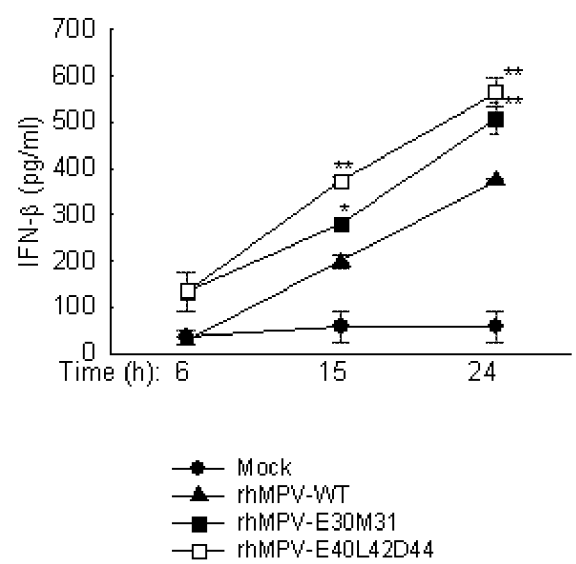

The present invention in general relates to the construction and characterization of novel Pneumoviridae strains that are both attenuated and immunogenic. In particular, human metapneumovirus (hMPV) and human respiratory syncytial virus (hRSV) strains that contain mutations within a single PDZ motif of M2-2 maintain an important immunogenic epitope as well as F and G protein expression and function. These strains and compositions containing these strains may be used to treat or prevent infections elicited by species of the Pneumoviridae family, in particular hMPV and (hRSV), which are the causative agents of lower and upper respiratory infections.

Before describing the invention in further detail, the following definitions are provided:

An "adjuvant" refers to a substance that enhances an immune response, e.g., an antibody or cell-mediated immune response against a specific agent, e.g., an antigen, or an infectious agent.

An "attenuated" virus strain refers a mutated or modified or recombinant virus having reduced or no virulence or propensity to cause a disease or infection normally associated with the "wild-type" or "unmodified" (or in this case "non-mutated") virus.

An "attenuated" Pneumoviridae vaccine strain in particular refers to a Pneumoviridae strain that has been modified to have reduced or no virulence or propensity to cause a disease or infection which is normally associated with a "wild-type" or "unmodified" (or in this case "non-mutated") virus, in particular lower and/or upper respiratory infections. More particularly, this includes "attenuated" Pneumoviridae vaccine strains that are "modified" or "altered" or "mutated" to contain at least one mutation in at least one PDZ motif of M2-2, preferably two or more mutations, e.g., 2 mutations or 3 mutations, in a single PDZ motif of M2-2. The mutations are site-specific mutations that do not delete all or part of the PDZ motifs and/or M2-2. Instead, the mutation(s) disrupt the expression or functionality of M2-2, wherein such live attenuated Pneumoviridae strain elicits immunoprotection against the virus, i.e., maintains an important immunogenic epitope. Notably, the attenuated strains also maintain the function of the F and G proteins.

"Pneumoviridae infection" or "infection elicited by Pneumoviridae" herein refers to the infection of a susceptible host with a Pneumoviridae virus, e.g. human metapneumovirus (hMPV), human respiratory syncytial virus (hRSV), a bovine respiratory syncytial virus (BRSV), an ovine respiratory syncytial virus (ORSV), or an avian metapneumovirus (AMPV), e.g., preferably hMPV and hRSV, and diseases associated therewith including lower and/or upper respiratory infections.

"M2-2" or "M2" herein refers to a protein encoded by the "M2" gene found in species of the Pneumoviridae family, e.g., hMPV and hRSV. M2-2 is involved in the regulation of viral RNA transcription and replication. In hRSV, the M2-2 protein suppresses viral mRNA synthesis, while in hMPV M2-2 has a stimulatory role in mRNA transcription. The M2-2 sequence also differs between hMPV and hRSV, but both M2-2 proteins contain PDZ motifs. M2-2 is highly conserved (>90%) between the two hMPV strains, A and B[15]. The M2-2 of Canadian isolate hMPV83, which belongs to A2 strain, has about 70 amino acids. The domains of M2-2 responsible for the immune inhibition are located in last 45 amino acids, which also promote viral genome replication and contain a cytotoxic T-lymphocyte (CTL) epitope[8,16-18]. The first 25 amino acids of M2-2 are solely responsible for promoting viral gene transcription[8].

"Reduced expression of M2-2" herein means that a Pneumoviridae strain expresses less of the gene product encoded by the M2 gene relative to a corresponding wild-type or unmodified Pneumoviridae strain, e.g., it expresses at least 10, 20, 30, 40, 50, 60, 70, 80, 90, 95 or 99% less of the protein compared to a corresponding wild-type or unmodified Pneumoviridae strain, e.g., a hMPV or hRSV strain. The reduced expression is a result of the site-specific mutations that disrupt the expression or functionality of M2-2 but do not delete all or part of the PDZ motifs and/or M2-2.

"Reduced functionality" or "reduced functionality of M2-2" means that the Pneumoviridae strain contains one or more mutations that inhibit or eliminate a function associated with M2-2. In particular, mutations within the PDZ domains of M2-2 may disrupt the inhibition of M2-2-mediated immune evasion. For example, strains with reduced functionality (as a result of, e.g., one or more mutations in a PDZ motif of M2-2) may disrupt the ability of M2-2 to block the interaction of MAVS and its downstream adaptors, e.g., TRAF, thus weakening the M2-2-mediated inhibition of MAVS signaling.

"M2-2-mediated immune evasion" herein refers to inter alia the use of M2-2 PDZ motifs to launch immune evasion, e.g., hMPV and hRSV immune evasion, by blocking the interaction of MAVS and TRAF adaptors. M2-2 contributes to immune evasion by targeting mitochondrial antiviral-signaling protein (MAVS), which is an antiviral signaling molecule, and prevent downstream adaptors (e.g., TRAF family members, e.g., TRAF3, TRAF5, and/or TRAF6) from being recruited to MAVS. TRAFs are important for activating transcription factors NF-κB and/or IRF-3.

"Disruption of M2-2-mediated immune evasion" herein refers to mutation(s) in a PDZ-binding motif of M2-2 that alter the normal ability of M2-2 to mediate immune evasion. Disruption may be characterized by one or more of M2-2-mediated suppression of immune gene expression in response to infection is reduced as compared to a wild-type (or "non-mutated") strain; M2-2-mediated enhancement of viral genome replication in response to infection is reduced as compared to a wild-type (or "non-mutated") strain; enhanced IRF-3 nuclear translocation; enhanced p65 nuclear translocation; increased chemokine gene expression; increased cytokine gene expression; and increased dendritic cell and/or T cell migration and maturation. Exemplary chemokines and cytokines that are increased upon disruption of M2-2-mediated immune evasion include, but are not limited to, IL-1α, IL-1β, IL-6, IL-12, IFN-β, IFN-γ, G-CSF, GM-CSF, TNF-α, KC, MCP-1, MIP-1α, MIP-1β, and RANTES.

"Human metapneumovirus ΔM2-2 strains" herein refers to a specific attenuated hMPV vaccine strains containing point mutations in M2 that alter the expression and/or function of the M2 gene. Specific examples of such strains include "rhMPV-E30M31" and "rhMPV-E40L42D44" which contain point mutations in a PDZ motif within the last 45 amino acids of the protein. The immune inhibitory domains of M2-2 are located in the last 45 amino acids, which also regulate viral genome replication. The PDZ-binding motifs in the last 45 amino acids are 29-DEMI-32 (SEQ ID NO:16), 39-KEALSDGI-46 (SEQ ID NO:17), 58-LENI-61 (SEQ ID NO:18) and 61-1E11-64 (SEQ ID NO:19). "rhMPV-E30M31" contains mutations at E30 and M31 of the PDZ motif having the amino acids sequence 29-DEMI-32 (SEQ ID NO:16). "rhMPV-E40L42D44" contains mutations at E40, L42 and D44 of the PDZ motif having the amino acids sequence 39-KEALSDGI-46 (SEQ ID NO:17).

A "variant" of rhMPV-E30M31 or rhMPV-E40L42D44 herein refers to a rhMPV-E30M31 or rhMPV-E40L42D44 strain that has been modified in some manner, e.g., to include another genetic modification, e.g., another attenuating mutation or modification which further reduces virulence or infectivity such as the deletion or modification of another gene the expression of which may affect the persistence of the strain in a susceptible host or its virulence in a susceptible host.

An "immunogenic composition" herein refers to a composition containing an attenuated strain of the Pneumoviridae family, e.g., hMPV or hRSV, which elicits an immune response in a susceptible host, e.g., a $T_h1$ response, a Th2 response, and/or a cellular (e.g., T and/or DC cell-mediated) immune response.

A "vaccine" herein refers to a composition containing an attenuated Pneumoviridae strain according to the invention which elicits a therapeutic or prophylactic immune response against a species of the Pneumoviridae family, preferably hMPV or hRSV.

A "pharmaceutically acceptable carrier" or "excipient" refers to compounds or materials conventionally used in immunogenic or vaccine compositions during formulation and/or to permit storage.

"Prophylactically effective amount" of a live attenuated Pneumoviridae strain according to the invention refers to an amount sufficient to prevent or reduce the incidence of infection in a susceptible host.

"Therapeutically effective amount" of a live attenuated Pneumoviridae strain according to the invention refers to an amount sufficient to treat Pneumoviridae infection or a disease associated therewith in a susceptible host.

A "susceptible host" herein refers to a host or animal that may be infected by a species of the Pneumoviridae family. Such hosts include humans, e.g., an infant (under 2 years of age), a child (under 18 years of age) or an elderly person (over 60 years of age), which may be infected by hMPV and/or hRSV, or non-humans, e.g., laboratory animals (such as mouse, rat, guinea pig, rabbit, and non-human primates), companion animals (such as horses, cats and dogs), and livestock (such as cows, turkeys, chicken, and sheep). BRSV, ORSV, and AMPV are exemplary Pneumoviridae that infect companion animals and livestock. Indeed, it is possible that these viruses can infect animals across species since, e.g., BRSV antibodies have been found in horses, cats, and dogs.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism. The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as an isolated virus or protein or nucleic acid) refers to a component that has been substantially separated or purified away from its environment or other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The term "recombinant" means a polynucleotide with semisynthetic or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter. The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Having provided the foregoing definitions, the invention is now further described.

The invention relates to mutants of hMPV that contain altered PDZ regions of M2-2 that possess a reduced ability to inhibit MAVS-mediated antiviral signaling and, thus, can be utilized as effective live attenuated vaccines against hMPV. The mutation scheme, i.e., site-specific mutation of a PDZ motif within M2-2, is also applicable in the homologous region of hRSV and other species of the Pneumoviridae family, e.g., bovine respiratory syncytial virus (BRSV), ovine respiratory syncytial virus (ORSV), and avian metapneumovirus (AMPV) among others.

A mutation can be, but is not limited to, a deletion of one or more amino acids, an addition of one or more amino acids, a substitution (conserved or non-conserved) of one or more amino acids or a combination thereof. As used herein, the mutation or mutation scheme is preferably a substitution (conserved or non-conserved) of one or more amino acids or a combination thereof.

hMPV can be mutated, e.g., using point mutations, such that the infectivity of hMPV is reduced. In certain embodiments, the infectivity of hMPV is reduced by a factor of at least 5, 10, 50, 100, 500, 10, $5\times10^3$, $10^4$, $5\times10^4$, $10^5$, $5\times10^5$, or at least $10^6$.

Additionally, hMPV can be mutated, e.g., using point mutations, such that the rate of replication of the recombinant virus is reduced or increased. The rate of replication can be determined by any standard technique known to the skilled artisan. The rate of replication is represented by the growth rate of the virus and can be determined by plotting the viral titer over the time post infection. The viral titer can be measured by any technique known to the skilled artisan. In certain embodiments, a suspension containing the virus is incubated with cells that are susceptible to infection by the virus including, but not limited to, Vero cells, LLC-MK-2 cells, Hep-2 cells, LF 1043 (HEL) cells, MRC-5 cells, WI-38 cells, tMK cells, 293 T cells, QT 6 cells, QT 35 cells, or chicken embryo fibroblasts (CEF). Subsequent to the incubation of the virus with the cells, the number of infected cells is determined. In certain specific embodiments, the virus comprises a reporter gene. Thus, the number of cells expressing the reporter gene is representative of the number of infected cells. In a specific embodiment, the virus comprises a heterologous nucleotide sequence encoding for eGFP, and the number of cells expressing eGFP, i.e., the number of cells infected with the virus, is determined using FACS.

The assays described herein may be used to assay viral titre over time to determine the growth characteristics of the virus. In a specific embodiment, the viral titre is determined by obtaining a sample from the infected cells or the infected subject, preparing a serial dilution of the sample and infecting a monolayer of cells that are susceptible to infection with the virus at a dilution of the virus that allows for the emergence of single plaques. The plaques can then be counted and the viral titre express as plaque forming units per milliliter of sample. In a specific embodiment of the invention, the growth rate of a virus of the invention in a subject is estimated by the titer of antibodies against the virus in the subject. Without being bound by theory, the antibody titer in the subject reflects not only the viral titer in the subject but also the antigenicity. If the antigenicity of the virus is constant, the increase of the antibody titer in the subject can be used to determine the growth curve of the virus in the subject. In a preferred embodiment, the growth rate of the virus in animals or humans is best tested by sampling biological fluids of a host at multiple time points post-infection and measuring viral titer.

The expression of heterologous gene sequence in a cell culture system or in a subject can be determined by any technique known to the skilled artisan. In certain embodiments, the expression of the heterologous gene is measured by quantifying the level of the transcript. The level of the transcript can be measured by Northern blot analysis or by RT-PCR using probes or primers, respectively that are specific for the transcript. The transcript can be distinguished from the genome of the virus because the virus is in the antisense orientation whereas the transcript is in the sense orientation. In certain embodiments, the expression of the heterologous gene is measured by quantifying the level of the protein product of the heterologous gene. The level of the protein can be measured by Western blot analysis using antibodies that are specific to the protein.

In certain embodiments, the invention provides a live attenuated hMPV strain comprising a genetic modification at one or more of the amino acid positions selected from the group consisting of: position 30 and/or position 31 of M2 [E30 and/or E31 of the PDZ motif 29-DEMI-32, SEQ ID NO:16]; and position 40, 42, and/or 44 of M2 [E40, L42, and/or D44 of the PDZ motif 39-KEALSDGI-46, SEQ ID NO:17].

In addition to mutations within the PDZ motif of M2-2, the attenuated virus may also contain other mutations including, but not limited to, replacing a gene of the human virus with the analogous gene of a virus of a different species (e.g., of RSV, APV, PIV3 or mouse pneumovirus), of a different subgroup, or of a different variant. In illustrative embodiments, the N-gene, the P-gene, the M-gene, the F-gene, the SH-gene, the G-gene or the L-gene of a mammalian MPV is replaced with the N-gene, the P-gene, the M-gene, the F-gene, the SH-gene, the G-gene or the L-gene, respectively, of an APV. In other illustrative embodiments, the N-gene, the P-gene, the M-gene, the F-gene, the SH-gene, the G-gene or the L-gene of APV is replaced with the N-gene, the P-gene, the M-gene, the F-gene, the SH-gene, the G-gene or the L-gene, respectively, of a mammalian MPV.

In some embodiments, other mutations may be introduced into the virus (e.g., missense mutations) can be introduced into the N-gene, the P-gene, the M-gene, the F-gene, the M2-gene, the SH-gene, the G-gene or the L-gene of the recombinant virus. Also, the mutations may include additions, substitutions, deletions, or combinations thereof. For example a deletion mutation in any of the N, P, L, F, G, M2-1, or other M2 proteins may be introduced. In other embodiments, a missense mutation may be introduced which results in a cold-sensitive mutation or a heat-sensitive mutation. In some embodiments, major phosphorylation sites of P protein of the virus may be removed. In another embodiment, a mutation or mutations are introduced into the L gene of the virus to generate a temperature sensitive strain. In yet another embodiment, the cleavage site of the F gene is mutated in such a way that cleavage does not occur or occurs at very low efficiency.

In other embodiments, deletions (in addition to the site-specific mutations that disrupt the expression or functionality of M2) are introduced into the genome of the recombinant virus. In more specific embodiments, a deletion can be introduced into the N-gene, the P-gene, the M-gene, the F-gene, the SH-gene, the G-gene or the L-gene of the recombinant virus. In other specific embodiments, the deletion is in the SH-gene of the recombinant virus of the present invention.

In certain embodiments, the intergenic region of the recombinant virus is altered. In one embodiment, the length of the intergenic region is altered. In another embodiment, the intergenic regions may be shuffled from 5' to 3' end of the viral genome. In other embodiments, the genome position of a gene or genes of the recombinant virus can be changed. In one embodiment, the F or G gene is moved to the 3' end of the genome. In another embodiment, the N gene is moved to the 5' end of the genome.

In certain embodiments, attenuation of the virus is further enhanced by replacing a gene of the wild type virus with a gene of a virus of a different species, of a different subgroup, or of a different variant. In illustrative embodiments, the N-gene, the P-gene, the M-gene, the F-gene, the SH-gene, the G-gene or the L-gene of a mammalian MPV is replaced with the N-gene, the P-gene, the M-gene, the F-gene, the SH-gene, the G-gene or the L-gene, respectively, of an APV.

In other illustrative embodiments, the N-gene, the P-gene, the M-gene, the F-gene, the SH-gene, the G-gene or the L-gene of APV is replaced with the N-gene, the P-gene, the M-gene, the F-gene, the SH-gene, the G-gene or the L-gene, respectively, of a mammalian MPV. In one embodiment, attenuation of the virus is further enhanced by replacing one or more polymerase associated genes (e.g., N, P, L or M2) with genes of a virus of a different species.

In certain embodiments, attenuation of the virus may be further enhanced by replacing one or more specific domains of a protein of the wild type virus with domains derived from the corresponding protein of a virus of a different species.

For example, the ectodomain of an F protein of APV is replaced with an ectodomain of an F protein of a mammalian MPV.

The attenuated phenotypes of a recombinant virus of the invention can be tested by any method known to the artisan. A candidate virus can, for example, be tested for its ability to infect a host or for the rate of replication in a cell culture system. In certain embodiments, growth curves at different temperatures are used to test the attenuated phenotype of the virus. For example, an attenuated virus is able to grow at 35° C., but not at 39° C. or 40° C. In certain embodiments, different cell lines can be used to evaluate the attenuated phenotype of the virus. For example, an attenuated virus may only be able to grow in monkey cell lines but not the human cell lines, or the achievable virus titers in different cell lines are different for the attenuated virus. In certain embodiments, viral replication in the respiratory tract of a small animal model, including but not limited to, hamsters, cotton rats, mice and guinea pigs, is used to evaluate the attenuated phenotypes of the virus. In other embodiments, the immune response induced by the virus, including but not limited to, the antibody titers (e.g., assayed by plaque reduction neutralization assay or ELISA) is used to evaluate the attenuated phenotypes of the virus. In a specific embodiment, the plaque reduction neutralization assay or ELISA is carried out at a low dose. In certain embodiments, the ability of the recombinant virus to elicit pathological symptoms in an animal model can be tested. A reduced ability of the virus to elicit pathological symptoms in an animal model system is indicative of its attenuated phenotype. In a specific embodiment, the candidate viruses are tested in a monkey model for nasal infection, indicated by mucous production.

Various assays can be used to test the safety of a vaccine. For example, sucrose gradients and neutralization assays can be used to test the safety. A sucrose gradient assay can be used to determine whether a heterologous protein is inserted in a virion. If the heterologous protein is inserted in the virion, the virion should be tested for its ability to cause symptoms even if the parental strain does not cause symptoms. Without being bound by theory, if the heterologous protein is incorporated in the virion, the virus may have acquired new, possibly pathological, properties.

Attenuated virus produced according to the invention will be used to confer prophylactic or therapeutic protection in susceptible hosts against Pneumoviridae infection, e.g., to treat or prevent lower and/or upper respiratory infection. The attenuated Pneumoviridae strain may be formulated using known techniques for formulating attenuated viral vaccines or immunogenic compositions of viral vaccines.

The immunogenic compositions of the present invention may be administered in a number of ways depending upon whether local or systemic treatment is desired.

Administration may be topical, parenteral, or enteral.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intranasal, intrasternal, intravenous, intraarterial, intrathecal, intraventricular, intraurethral, intracranial, intrasynovial injection or infusions; and kidney dialytic infusion techniques.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, drops, aerosols, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

The terms "oral", "enteral", "enterally", "orally", "non-parenteral", "non-parenterally", and the like, refer to administration of a compound or composition to an individual by a route or mode along the alimentary canal. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories for the lower intestinal tract of the alimentary canal.

Preferably, the formulated virus containing composition is suitable for intranasal, injection, topical or oral administration, for example as a dried stabilized powder for reconstitution in a suitable buffer prior to administration or in an aerosol composition. In a preferred embodiment, the composition is intranasally administered.

In some preferred exemplary embodiments the virus strain or immunogenic composition containing is intranasally administered by an intranasal delivery means which provides for topical or systemic delivery of the virus strain or immunogenic composition. For example the virus strain or immunogenic composition may be delivered using drops or a spray or aerosol formulation e.g., using a mechanical liquid spray pump or an inhaler, e.g., a pressurized metered-dose inhaler (pMDI) for nasal use.

Therefore, the invention includes a virus strain or composition containing according to any to the invention which is adopted for intranasal delivery, optionally for topical or systemic delivery of the virus strain or composition containing. For example, a virus strain or immunogenic composition according to the invention may be comprised in the forms of drops, spray or aerosol which in turn may be comprised in a mechanical liquid spray pump or an inhaler or other intranasal delivery device, e.g., a pressurized metered-dose inhaler (pMDI) suitable for nasal use.

Pharmaceutical compositions and formulations for topical administration may include transdermal patches, ointments, lotions, creams, gels, drops, suppositories, sprays, laerosols, iquids, semi-solids, monophasic compositions, multiphasic compositions (e.g., oil-in-water, water-in-oil), foams microsponges, liposomes, nanoemulsions, aerosol foams, polymers, fullerenes, and powders (see, e.g., Taglietti et al. (2008) Skin Ther. Lett. 13:6-8). Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal, or intraventricular administration may include sterile aqueous solutions that may also contain buffers, diluents and other suitable additives such as, but not limited to, penetration enhancers, carder compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, aerosols, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

The compositions of the present invention may include excipients known in the art. Examples of excipients used for vaccine formulation such as adjuvants, stabilizers, preservatives, and trace products derived from vaccine manufacturing processes include but are not limited to: Aluminum Hydroxide, Amino Acids, Benzethonium Chloride, Formaldehyde or Formalin, Inorganic Salts and Sugars, Vitamins, Asparagine, Citric Acid, Lactose, Glycerin, Iron Ammonium Citrate, Magnesium Sulfate, Potassium Phosphate, Aluminum Phosphate, Ammonium Sulfate, Casamino Acid, Dimethyl-betacyclodextrin, 2-Phenoxyethanol, Bovine Extract, Polysorbate 80, Aluminum Potassium Sulfate, Gelatin, Sodium Phosphate, Thimerosal, Sucrose, Bovine Protein, Lactalbumin Hydrolysate, Formaldehyde or Formalin, Monkey Kidney Tissue, Neomycin, Polymyxin B, Yeast Protein, Aluminum Hydroxyphosphate Sulfate, Dextrose, Mineral Salts, Sodium Borate, Soy Peptone, MRC-5 Cellular Protein, Neomycin Sulfate, Phosphate Buffers, Polysorbate, Bovine Albumin or Serum, DNA, Potassium Aluminum Sulfate, Amorphous Aluminum Hydroxyphosphate Sulfate, Carbohydrates, L-histidine, Beta-Propiolactone, Calcium Chloride, Neomycin, Ovalbumin, Potassium Chloride, Potassium Phosphate, Sodium Phosphate, Sodium Taurodeoxychoalate, Egg Protein, Gentamicin, Hydrocortisone, Octoxynol-10, α-Tocopheryl Hydrogen Succinate, Sodium Deoxycholate, Sodium Phosphate, Beta-Propiolactone, Polyoxyethylene 910, Nonyl Phenol (Triton N-101, Octoxynol 9), Octoxinol-9 (Triton X-100), Chick Kidney Cells, Egg Protein, Gentamicin Sulfate, Monosodium Glutamate, Sucrose Phosphate Glutamate Buffer Calf Serum Protein, Streptomycin, Mouse Serum Protein, Chick Embryo Fibroblasts, Human Albumin, Sorbitol, Sodium Phosphate Dibasic, Sodium Bicarbonate, Sorbitol, Sucrose, Potassium Phosphate Monobasic, Potassium Chloride, Potassium Phosphate Dibasic, Phenol, Phenol Red (Phenolsulfonphthalein), Amphotericin B, Chicken Protein, Chlortetracycline, Ethylenediamine-Tetraacetic Acid Sodium (EDTA), Potassium Glutamate, Cell Culture Media, Sodium Citrate, Sodium Phosphate Monobasic Monohydrate, Sodium Hydroxide, Calcium Carbonate, D-glucose, Dextran, Ferric (III) Nitrate, L-cystine, L-tyrosine, Magnesium Sulfate, Sodium Hydrogenocarbonate, Sodium Pyruvate, Xanthan, Peptone, Disodium Phosphate, Monosodium Phosphate, Polydimethylsilozone, Hexadecyltrimethylammonium Bromide Ascorbic Acid, Casein, Galactose, Magnesium Stearate, Mannitol, Hydrolyzed Porcine Gelatin, Freund's emulsified oil adjuvants (complete and incomplete), Arlacel A, Mineral oil, Emulsified peanut oil adjuvant (adjuvant 65), *Corynebacterium granulosum*-derived P40 component, Lipopolysaccharide, *Mycobacterium* and its components, Cholera toxin, Liposomes, Immunostimulating complexes (ISCOMs), Squalene, and Sodium Chloride.

The vaccine or immunogenic composition may be used in the vaccination of a mammalian host, particularly a human, cow, sheep, horse, cat, dog, turkey or other suitable non-human host. A dosage may comprise at least $10^4$ pfu, $5\times10^4$ pfu, $10^5$ pfu, $5\times10^5$ pfu, $10^6$ pfu, $5\times10^6$ pfu, $10'$ pfu, $5\times10^7$ pfu, $10^8$ pfu, or $5\times10^8$ pfu of said live attenuated Pneumoviridae strain. In some instances the subject may be immunocompromised or may comprise another condition, e.g., another type of infection, e.g., infection with both hMPV and hRSV.

The experimental details of these experiments are described in more detail in the following examples. These examples are offered to illustrate, but not to limit, the claimed invention.

EXAMPLES

Example 1: Construction of hMPV-WT Antigenome, M2-2 Mutant Antigenome and M2-2 Plasmid and Statistical Analyses hMPV antigenome plasmid construction: A plasmid encoding hMPV antigenome was constructed as described in Biacchesi et al. (Virology. 2004; 321:247-59) with some modifications. In brief, three overlapping cloned sub-genomic fragments were created and ligated sequentially into an anti-genomic cDNA expression vector pBSKSII:Fragment 1 contained the leader and the putative N, P, and M genes, bordered on the upstream end by a T7 RNA polymerase promoter (T7p) and on the downstream end by an NheI site that was created by four nucleotide substitutions in the putative M-F intergenic region as a marker to distinguish between cDNA-derived and biologically derived HMPV. Three non-viral G residues were added to the 5' end of the antigenome to enhance promoter efficiency. Fragment 2 included F, M2, SH, and G genes and was bordered on the upstream side by the added NheI site and on the downstream side by a naturally occurring Acc65I site. Fragment 3 consisted of polymerase L gene and trailer sequence, bordered on the upstream side by the Acc65I site and on the downstream side by part of the hepatitis delta virus ribozyme sequence ending in an RsrII site that occurs naturally within the ribozyme. The anti-genomic cDNA was cloned in vector pBSKSII, which supplied the remainder of the hepatitis delta virus ribozyme followed by a terminator for T7 RNA polymerase (T7t). The sequence of the complete assembled cDNA was confirmed in its entirety, showing that the encoded antigenome (13 335 nt long, exclusive of non-viral nt) differed from the consensus sequence of biologically derived HMPV83. To clone the sub-genomic regions, viral RNA was purified from hMPV CAN83-infected LLC-MK2 cells using QIAamp viral RNA kit (Qiagen, Alameda, Calif.). First strand cDNA was then generated using Superscript III reverse transcriptase (Invitrogen Carlsbad, Calif.). PCR was carried out using Pfu DNA polymerase (Stratagene, La Jolla, Calif.) following manufacturer's instruction. Fragment I was first cloned using forward primer: 59-ACGCGAAAAAAACGCGTATAAATTAAGTTAC-39, SEQ ID NO:1 and reverse primer: 59-TTTGTCCCGTTCTTGATTgctAgCATTCTTATTCTAACTTg-39, SEQ ID NO:2. The cloned fragment which contains the putative N, P, and M genes was first cloned into TOPO cloning vector (Invitrogen, Carlsbad, Calif.). On the downstream end of this fragment, a NheI site was created by four nucleotide substitutions in the putative M-F intergenic region as a marker to distinguish between cDNA-derived and biologically derived hMPV. In order to insert a T7 RNA polymerase promoter (T7p) at the 39 end of the antigenome, fragment I inserted TOPO was used as template to clone the T7p-fragment I using same reverse primer and forward primer:

SEQ ID NO: 3

59-*cgcgacgtc*TAATACGACTCACTATAGGGACGCGAAAAAAACGCGTA

TAAATTAAGTTAC-39.

Italicized letters indicate restriction enzyme site. Underlined letters indicate T7 RNA polymerase promoter (T7p) sequence. Construction of fragment II, which contains F, M2, SH and G), was cloned using forward primer: gaatgctAgCAATCAAGAACGGGAC (SEQ ID NO:4) and reverse primer: tgttGGTACCTACATGTTTTACTTTAGAGC (SEQ ID NO:5). For the fragment III, containing L and part of the hepatitis delta virus ribozyme, was cloned using respective forward and reverse primers:

(SEQ ID NO: 6)

tgta*GGTACC*AACAATCAAGAAACCAAAAG and (SEQ ID NO: 7)

ggt*cggacc*gcgaggaggtggagatgccatgccgacccACGGCAAAAAAA

CCGTATACATTC.

Italicized letters indicate restriction enzyme site. The cloned fragments in TOPO vectors was sub-cloned sequentially intot pBSKSII vector (a gift from Dr. Buchholz, NIAID, Bethesda) to have a complete hMPV antigenome expression vector.

M2-2 mutant rhMPV construction: Construction of M2-2 mutant cDNA was performed similarly to Ren et al. (J Virol. 2012 Sep. 26; 86(23):13049-61) ("Ren") and Bao et al. (Plos One. 2013 April; 8(4):e62568) ("Bao"). We used site-directed mutagenesis to individually mutate two PDZ motifs of M2-2 in the second segment, followed by the replacement of WT segment with the mutated one. The multiple-site mutagenesis does not affect M2-1 codons. Primer sequence for generating M2-2 E30M31 mutant antigenome is CTATAGAGGTTGATGCAGCGATATGGACTCAAAAAGAA (SEQ ID NO:8). The primer to generate M2-2 E40L42D44 mutant is CAAAAAGAATTAAAAGCAGCTGCGTCCGCAGGGATAGTGAAGTCTTCACA (SEQ ID NO:9). Italicized letters indicate mutated sites. To recover recombinant hMPV, confluent BSR T7/5 cells in six-well dishes were transfected with 5 µg of anti-genomic plasmid corresponding to rhMPV-WT or -M2-2 mutant, together with plasmids encoding support proteins for recombinant virus recovery as previously described (5, 6). Trypsin (Worthington, Lakewood, N.J.) was added on day 3 post-transfection to a final concentration of 1 µg/ml, and then cell-medium mixtures were passed onto fresh LLC-MK2 cells and incubated at 35° C. Typical viral cytopathic effect (CPE) was usually observed around day 5 to 6 postinfection (P.i.).

Recombinant M2-2 mutant viruses were confirmed by sequencing of RT-PCR products of viral RNA. The recovered viruses were then amplified for two passages in LLC-MK2 cells and saved as stock viral preparations. Viruses with no more than 4-5 passages were used in all experiments.

Plasmid construction: To investigate the role of M2-2 motifs in regulating MAVS-mediated signaling in the overexpression system, site-directed mutagenesis was used. The primer sequences for generating M2-2 single protein mutants are the same as those for generating M2-2 mutant in anti-genomic system. The final M2-2 constructs were verified by sequencing performed by the protein chemistry core laboratory at UTMB.

Statistical Analysis: Statistical significance was determined using analysis of variance (ANOVA). P value of less than 0.05 was considered significant. Mean±standard error (SE) is shown.

Example 2: rhMPV-E30M31 and rhMPV-E40L42D44 Induce Greater Cytokine/Chemokine Secretion than Wild Type rhMPV Materials and Methods rhMPV strain construction: The PDZ motifs 29-DEMI-32 (SEQ ID NO:16) and 39-KEALSDGI-46 (SEQ ID NO:17) were mutated as in Example 1 to generate two recombinant hMPV strains (rhMPV) containing mutations in E30 and M31 of motif 29-DEMI-32 (SEQ ID NO:16) (rhMPV-E30M31) or in E40, L42 and D44 of motif 39-KEALSDGI-46 (SEQ ID NO:17) (rhMPV-E40L42D44).

Cell line and growing condition: A549, human alveolar type II-like epithelial cells were maintained in F-12K medium containing 10% (vol/vol) FBS, 10 mM glutamine, 100 IU/ml penicillin, and 100 µg/ml streptomycin.

Viral preparation, viral infection, and chemokine/cytokine detection: The isolate hMPVCAN-83 and its derived recombinant viruses were propagated in LLC-MK2 cells at 35° C. in the absence of serum and in the presence of 1 µg/ml of trypsin, and were sucrose purified, as previously described in (Bao et al., Plos Path. 2008 May; 4(5):e1000077). Viral titer was determined by immunostaining in LLC-MK2 cells, as previously described in (Bao et al., Plos Path. 2008 May; 4(5):e1000077). To characterize the growth pattern of recombinant M2-2 mutant viruses, LLC-MK2 or Vero cell monolayers in 6-well plate were infected with rhMPV, WT or individual mutants, at multiplicity of infection (MOI) of 0.1. An equivalent amount of sucrose solution was added to uninfected LLC-MK2 or Vero cells, as control (mock infection). After initial absorption, viral inoculum was removed and cells were supplied with fresh serum-free medium with trypsin. Viruses were harvested at different times p.i. and viral titer was determined by immunostaining in LLC-MK2 cells, as previously described in (Bao et al., Plos Path. 2008 May; 4(5):e1000077).

To investigate the role of interested M2-2 motifs in regulating innate antiviral signaling at the acute phase of infection, A549 cell monolayers were infected with rhMPV-WT or M2-2 mutant virus, at MOI of 2. Mock infection was used as negative control. Supernatants were harvested at different times p.i., and the concentrations of cytokines and chemokines were determined by ELISA or a multiplex immunoassay.

Results rhMPV-E30M31 and rhMPV-E40L42D44 induced greater secretion of several cytokines/chemokines than wild type (WT)-rhMPV at 15 and/or 24 h p.i. See FIG. 1A-G.

Example 3: Increased NF-κB and IRF-3 Activation by M2-2 Mutant rhMPV

Materials and Methods

Antibodies: Monoclonal antibodies against Lamin b were obtained from Sigma-Aldrich (Sigma, St. Louis, Mo.). Primary antibodies against phosphorylated IRF-3 and P65 were purchased from Millipore (Millipore, Billerica, Mass.). FITC-conjugated goat anti-rabbit antibody was from Zymed, San Francisco, Calif. Primary antibodies against IRF-3 and horseradish-coupled secondary antibodies were purchased from Santa Cruz (Santa Cruz, Santa Cruz, Calif.).

Cell lines, growing conditions, and viral infection: A549 cells were cultured as in Example 2. A549 cells in flasks were mock infected or infected with rhMPV-WT, rhMPV-E30M31, or rhMPV-E40L42D44, at MOI of 2, for various times as described in Example 2.

Preparation of nuclear fractions and detection of nuclear translocation of p65 and IRF-3: Total cells were lysed to prepare nuclear fractions, as previously described (Bao et al., Plos One. 2013 April; 8(4):e62568). Nuclear extracts of uninfected and infected cells were prepared using hypotonic/nonionic detergent lysis, according to Schaffner protocol (Schreiber et al., Nucleic Acids Res. 1989; 17:6419). To prevent contamination with cytoplasmic proteins, isolated nuclei were purified by centrifugation through 1.7 M sucrose buffer A for 30 min, at 12,000 rpm, before nuclear protein extraction, as previously described (Brasier et al., J Virol. 2004; 78:11461-76). Nuclear extracts were fractionated by SDS-PAGE, and transferred to polyvinylidene difluoride membranes. Western blots were used to assess the nuclear translocation of p65 and IRF-3. The expression of a nuclear protein lamin B, used as an internal control, was also compared among the group.

Western blots: Proteins were quantified with a protein quantification kit from Bio-Rad, followed by fractionation using SDS-PAGE denaturing or native gels and protein transferring to polyvinylidene difluoride membranes. Membranes were blocked with 5% milk in TBS-Tween 20 and incubated with the proper primary antibodies according to manufacturer's instruction.

Results

Figure 2A:
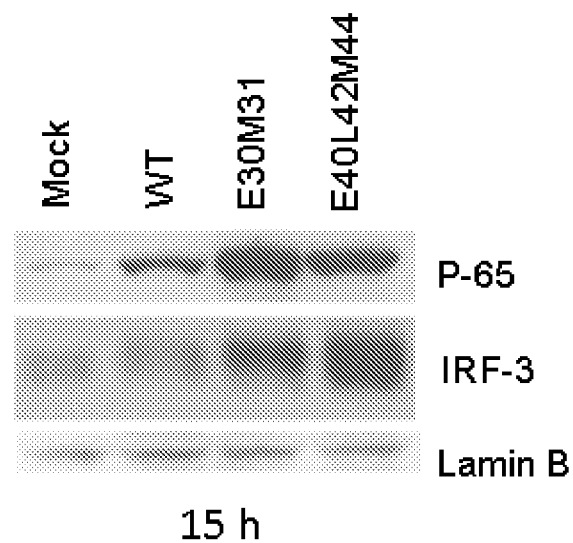
FIG. 2A-B contain data showing NF-κB and IRF-3 activation by rhMPV, measured at 15 h (Panel A) and 24 h (Panel B) post-infection. A549 cells in flasks were mock infected or infected with rhMPV-WT, rhMPV-E30M31, or rhMPV-E40L42D44, at MOI of 2, for various times as indicated. Nuclear fractions were prepared, followed by western blot to assess the nuclear translocation of p65 and IRF-3. The expression of a nuclear protein lamin B, used as an internal control, was also compared among the group.
Figure 2B:
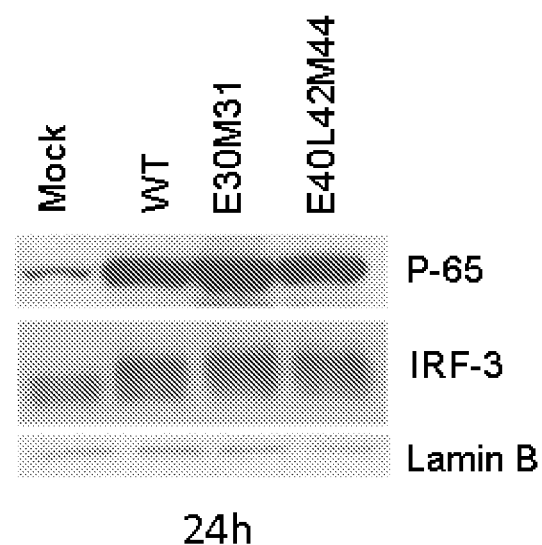

Among the IRF family, IRF-3 is necessary for IFN-β and RANTES gene expression in response to paramyxovirus infections. As expected, there was a significant increase in IRF-3 nuclear translocation in M2-2 mutant-infected cells, compared to rhMPV-WT-infected cells (See FIG. 2A-B).

P65, an important member of the NF-κB superfamily, is also important in the induction of chemokines and cytokines by viruses including paramyxovirus. The significant role of the M2-2 motifs in modulating hMPV-induced NF-κB activation was also confirmed by enhanced p65 nuclear translocation in mutant-infected A549 cells, compared to rhMPV-WT-infected cells (See FIG. 2A-B).

Example 4: Assaying Genome Replication and Viral Gene Transcription for M2-2 Mutant rhMPV Material and Methods Cell lines, growing conditions, and viral infection: A549 cells, grown as described in Example 2, were grown in 6-well plates. These cells were mock infected or infected with rhMPV mutants or WT at MOI of 2 for various periods of time, as in Example 2, followed by total RNA extraction using Trizol. The extracted RNAs in triplicate were then subjected to real-time PCR to assay genomic RNAs or viral G gene transcription.

Quantification of viral gene transcription in rhMPV-infected cells: To quantify differences in the G transcription among different rhMPV infection, WT vs M2-2 mutants, a relative quantitative method was used. The relative method quantifies differences in the expression level of a specific target (gene) between different samples. The data output is expressed as a fold change or a fold difference of expression levels. The RT primer to measure the transcription of the hMPV was G:

(SEQ ID NO: 10)
5'-CGTCTCAGCCAATCCCTGGTTTTTTTTTTTTCTAGTTTTGC-3'.

Primers were designed to incorporate a "tag" (underlined letters) as part of the assay due to self-priming exhibited by viral RNA[22]. The tag sequence was derived from the bacterial chloramphenicol resistance (Cm$^r$) gene. The sequence with bold letters is complementary to poly(A) tails of the transcribed hMPV G gene. The sequence in italic is G gene specific. At a 25° C. annealing temperature, the 10 nucleotides (nt) matching G-specific sequences would not be sufficient for a stable efficient priming of cDNA from an antigenome of hMPV (positive strand). On the other hand, 22 nucleotides matching transcribed N (12 T's and G-gene-specific nucleotides) are able to attain stable annealing to the transcribed G gene. The hMPV G forward primer was 5'-CATCAGTCCAGTCCGACAGC-3' (SEQ ID NO:11), and the reverse primer against hMPV tag was 5'-CGTCTCAGCCAATCCCTGG-3' (SEQ ID NO:12). QPCRs were run in the ABI 7500 sequence detection system under the standard default conditions: initial steps of 50° C. for 2 min and 95° C. for 10 min and PCR steps of 95° C. for 15 s and 60° C. for 1 min, for 40 cycles.

Quantification of viral genome copies in rhMPV-infected cells: To quantify viral antigenomic copies in the context of hMPV infection, synthetic transcripts of the genome were generated from Topo plasmid containing N-P-M genes, using the T7 MegaScript kit, following the digestion with PmeI. The reaction mixture was then treated with Turbo DNase and purified using the MegaScript kit. Primers were designed to span the N and P regions of the viral genome and incorporated a Cm$^r$ tag. First-strand cDNA was transcribed with a P-specific primer, (SEQ ID NO: 13)
5'-CGTCTCAGCCAATCCCTGGTGATTATGAGTAATTAAAAAATGGGA
CAAG-3'.

The underlined letters indicate the Cm$^r$ tag sequence. QPCRs were performed using the following primers: forward, 5'-CGTCTCAGCCAATCCCTGG-3' (SEQ ID NO:14), and reverse, 5'-GCTTCATTACCCAT-GAAAAGAATATC-3' (SEQ ID NO:15). RT-PCRs and QPCRs were performed as described above.

Results

Figure 3A:
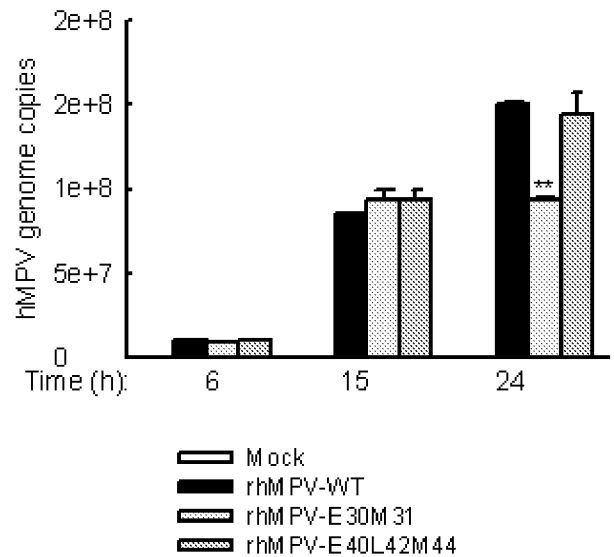
FIG. 3A-B contain data showing the replication and gene transcription characterization of recombinant viruses. A549 cells in 6-well plates were mock infected or infected with rhMPV at MOI of 2 for various periods of time as indicated, followed by total RNA extraction using Trizol. The extracted RNAs in triplicate were then subjected to real-time PCR to assay genomic RNAs (Panel A) or viral G gene transcription (Panel B). The results are the representative of two independent experiments and are expressed as mean±SE of absolute copy numbers of transcribed G gene or viral genome. **: $P<0.01$, relative to rhMPV-WT-infected A549 cells.
Figure 3B:
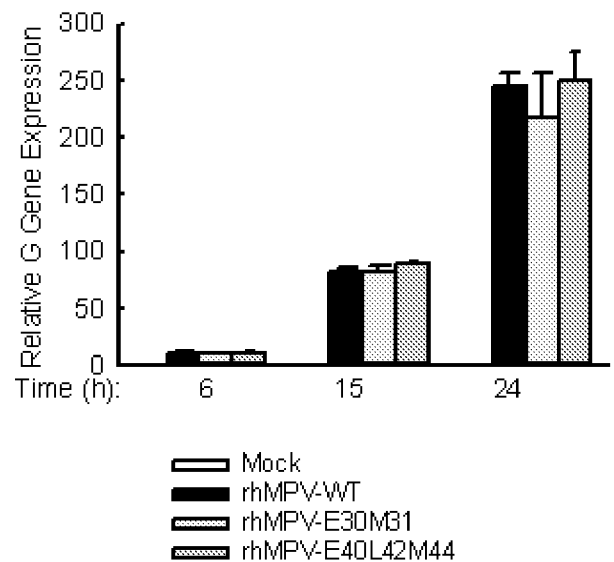

As shown in FIG. 3A-B, both mutants had similar genome copy numbers to WT virus following infection at the MOI of 2 at 15 h p.i. At 24 h p.i., rhMPV-E30M31-infected cells had many fewer virus genome copies than WT-infected cells. The mutations in the motif of 39-KEALSDGI-46 (SEQ ID NO:17), however, did not affect the genome replication at either time point.

As for the role of motifs in viral gene transcription, we found that both motifs were not involved in viral gene transcription (FIG. 3A-B). Since the expression of G, a previously described immune inhibitory viral protein, was not altered by amino acid mutations in motifs, the gene transcription results suggested a direct immune suppression by M2-2 motifs.

Example 5: Luciferase Reporting Assay

Materials and Methods

Cell lines and growing conditions: 293, a human embryonic kidney epithelial cell line (ATCC), was maintained in MEM containing 10% (vol/vol) FBS, 10 mM glutamine, 100 IU/ml penicillin, and 100 µg/ml streptomycin.

Figure 4:
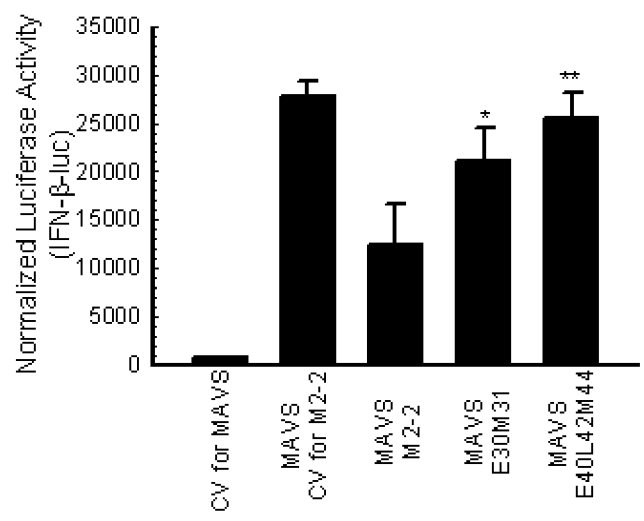
FIG. 4. contains data demonstrating the impact of motifs 29-DEMI-32 and 39-KEALSDGI-46 on M2-2-mediated immune evasion. A549 cells in triplicate were transfected with a luciferase reporter plasmid IFN-β-Luc (0.1 μg/well), a plasmid encoding MAVS or its control (0.1 μg/well), and a plasmid encoding hMPV M2-2 or its mutants, or a control vector (0.1 μg/well) were transfected. After 40 h, cells were harvested for luciferase activity measurement. *: P<0.05 and **: P<0.01 relative to MAVS+M2-2. CV: control vector for M2-2 or MAVS expression.

Transfection and reporter gene assay: Logarithmically-growing 293 were transfected in triplicate with 0.1 µg/well luciferase reporter gene plasmids containing IFN-β promoter (designated as IFN-β-Luc) or multiple copies of NF-κB binding sites (Kb-5-Luc), together with 0.1 µg/well plasmids encoding M2-2, WT or mutants, or their empty vector using FuGene 6 (Roche, Indianapolis, Ind.), as previously described (Bao et al., Plos Path. 2008 May; 4(5): e1000077). At 40 h post transfection, cells were lysed to independently measure luciferase and β-galactosidase reporter activity. Luciferase was normalized to the internal control β-galactosidase activity Results The importance of motifs in disrupting MAVS-mediated signaling was demonstrated by this luciferase reporter assay. MAVS-dependent IFN-β promoter activation was inhibited by M2-2 expression, while the inhibition was attenuated by the mutations in M2-2 motifs 29-DEMI-32 (SEQ ID NO:16) or 39-KEALSDGI-46 (SEQ ID NO:17) (FIG. 4). This experiment also suggested that M2-2-disrupted MAVS signaling is independent of virus infection.

Example 6: Determining the Role of TRAFs in hMPV-Induced Host Responses

Materials and Methods

Antibodies: Monoclonal antibodies against Lamin b were obtained from Sigma-Aldrich (Sigma, St. Louis, Mo.). The antibodies against TRAF2, TRAF3, and TRAF6 were from Cell Signaling, Danvers, Mass. Primary antibodies against phosphorylated IRF-3 and P65 were purchased from Millipore (Millipore, Billerica, Mass.). FITC-conjugated goat anti-rabbit antibody was from Zymed, San Francisco, Calif. Primary antibodies against TRAF5, IRF-3 and horseradish-coupled secondary antibodies were purchased from Santa Cruz (Santa Cruz, Santa Cruz, Calif.).

Cell lines, growing conditions, transfection, and infection: A549 cells were grown as in Example 2. A549 cells were then transfected with 100 nM siRNA targeting TRAF2 (siTRAF2), TRAF3 (siTRAF3), TRAF5 (siTRAF5), or TRAF6 (siTRAF6). A scrambled siRNA (siScr) was used as a negative control. At 48 h post transfection, cells were mock infected or infected with hMPV, as in Example 2, for 15 hours at a multiplicity of infection (MOI) of 2. Cells were harvested to prepare total cell lysates or nuclear fractions.

Isolation of nuclear fraction and total cell lysate: Nuclear fractions were isolated as in Example 3. Total cell lysates of uninfected and infected cells were prepared by adding ice-cold lysis buffer (50 mM Tric-HCl, pH 7.4, 150 mM NaCl, 1 mM EGTA, 0.25% sodium deoxycholate, 1 mM Na3VO4, 1 mM NaF, 1% Triton X-100 and 1 mg/ml of aprotinin, leupeptin and pepstatin). After incubation on ice for 10 min, the lysates were collected and detergent insoluble materials were removed by centrifugation at 4 uC at 14,000 g.

Western Blot: Nuclear extracts or total cell lysates were fractionated by SDS-PAGE, and transferred to polyvinylidene difluoride membranes. Membranes were blocked with 5% milk in TBS-Tween and incubated with the proper primary and secondary antibodies according to manufacturer's instruction. Nuclear fractions were used to assess the nuclear translocation of p65 and IRF-3. Membrane was stripped and reprobed with anti-O-actin or lamin-B antibody to control for equal loading of the total cell lysates or nuclear fractions respectively.

Measuring induction of cytokines/chemokines: Cells were prepared as detailed above. Supernatants were harvested to measure the induction of cytokines/chemokines by Bio-plex and/or ELISA, as in Example 2.

Results

Figure 5A:
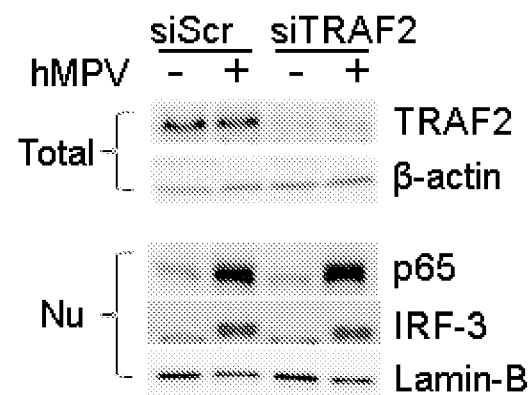
FIG. 5A-D contain data demonstrating the impact of TRAFs on hMPV-induced innate immunity. A549 cells were transfected with 100 nM siRNA targeting TRAF2 (siTRAF2) (Panel A), TRAF3 (siTRAF3) (Panel B), TRAF5 (siTRAF5) (Panel C), or TRAF6 (siTRAF6) (Panel D). A scrambled siRNA (siScr) was used as a negative control. At 48 h post transfection, cells were mock infected or infected with hMPV for 15 hours at a multiplicity of infection (MOI) of 2. Cells were harvested to prepare total cell lysates or nuclear fractions. Total cell lysates were subjected to 8% SDS-PAGE, followed by Western blot analysis of TRAFs expression. Nuclear fractions were used to assess the nuclear translocation of p65 and IRF-3. Membrane was stripped and reprobed with anti-β-actin or lamin-B antibody to control for equal loading of the total cell lysates or nuclear fractions respectively. Results are representative of three separate experiments.
Figure 5B:
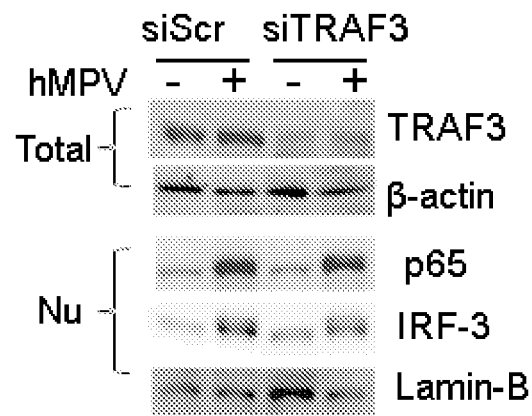
Figure 5C:
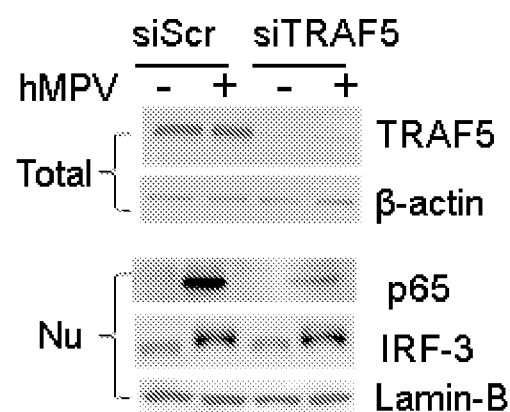
Figure 5D:
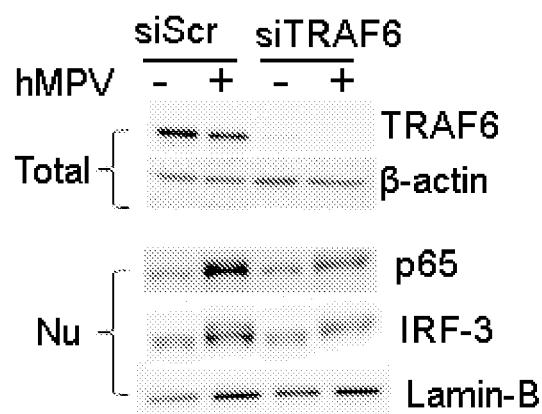
Figure 6A:
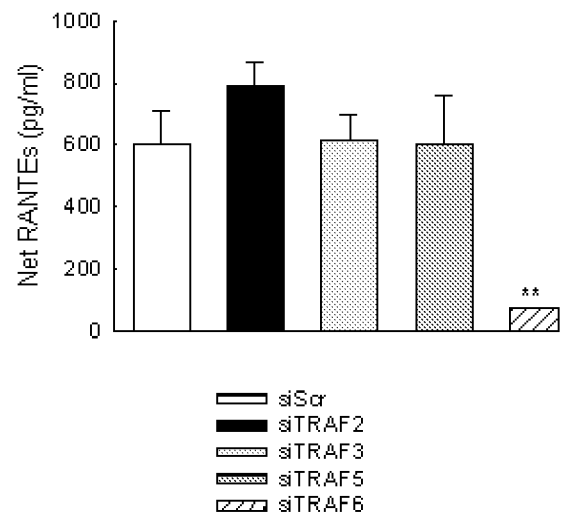
FIG. 6A-F contain data demonstrating the impact of TRAFs on hMPV-induced innate immunity. Cells were prepared as in FIG. 5A-D. Supernatants were harvested to measure the induction of cytokines/chemokines by Bio-plex and/or ELISA for the following cytokines/chemokines: RANTES (Panel A), TNF-α (Panel B), IP-10 (Panel C), IL-6 (Panel D), IFN-β (Panel E), and IL-8 (Panel F). Data shown are from three independent experiments and are expressed as mean±SE. *: P<0.05, and **: P<0.01, relative to siScr—treated A549 cells.
Figure 6B:
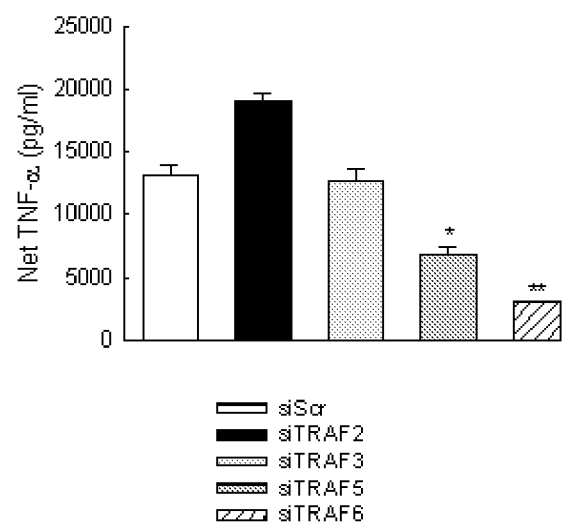
Figure 6C:
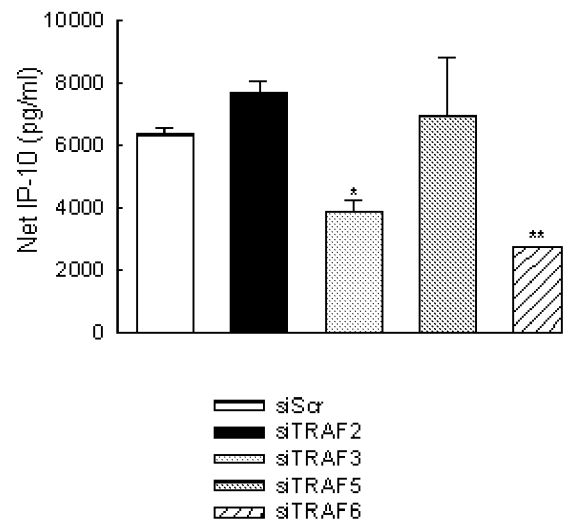
Figure 6D:
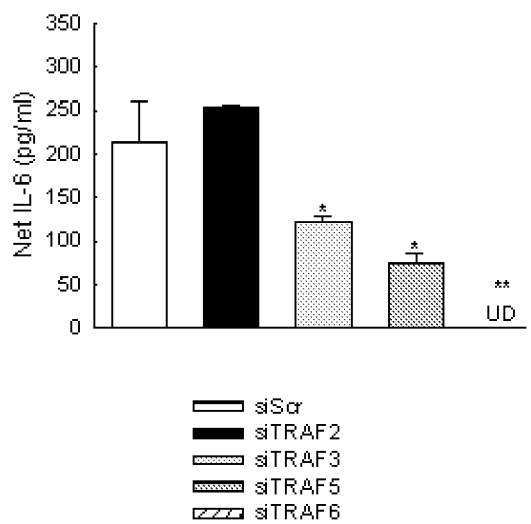
Figure 6E:
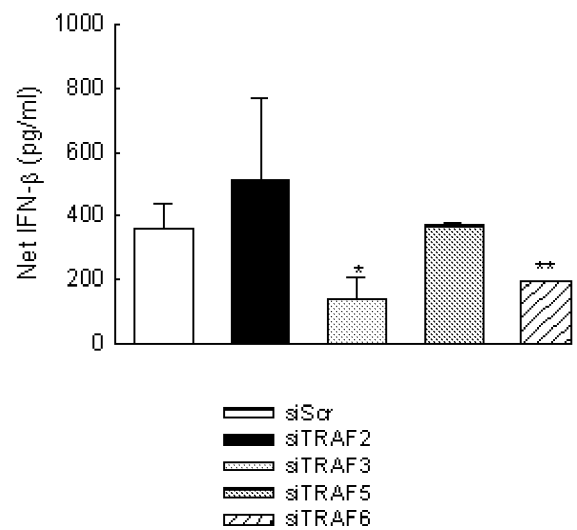
Figure 6F:
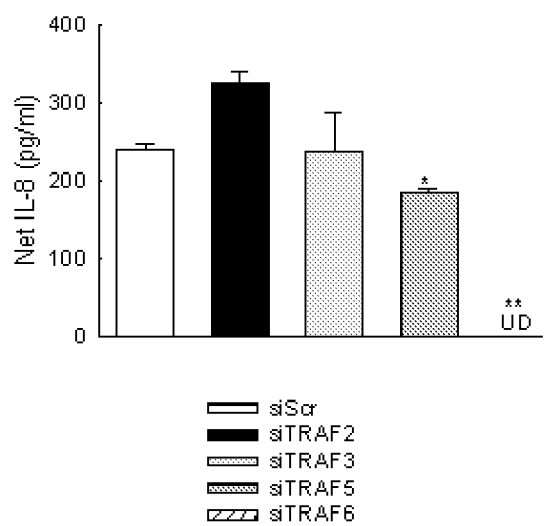

Treatment of A549 cells with siRNA targeting TRAFs effectively blocked the expression of each TRAF (>80%) (FIG. 5A-D), though individual TRAF suppression by siRNA did not affect the expression of the rest of the investigated TRAFs, suggesting that the expression of TRAFs is independent of each other. In response to hMPV, TRAF2 seemed not important in mediating the activation of p65 and IRF-3, two transcription factors critical for the induction of inflammatory/immune gene expression by hMPV (FIG. 5A). Consequently, TRAF2 did not affect hMPV-induced cytokines/chemokines (FIG. 6A-F). In contrast with TRAF2, TRAF6 had a broad and significant effect on hMPV-induced antiviral signaling, as TRAF6 suppression by its specific siRNA led to decreased activation of p65 and IRF-3 (FIG. 5D) and subsequently reduced secretion of proinflammatory and antiviral molecules (FIG. 6A-F). We also found that TRAF3 and TRAF5 contributed to the activation of IRF-3 and p65, respectively (FIG. 5B-C) confirming that the role of TRAFs in virus-mediated immune/inflammatory gene expression is isoform-specific.

Example 7: Measuring M2-2 Effect on TRAF5 Downstream Signaling

Materials and Methods

A549 cells were grown as in Example 2 and were then transfected with 0.5 µg/well luciferase reporter plasmid (NF-κB-Luc); 0.5 µg/well plasmid encoding TRAF5 or its control; and 0.1 µg/well plasmid encoding hMPV M2-2 or its mutants or a control vector. After 30 h, cells were harvested for luciferase activity measurement. Luciferase activity measured as in Example 5.

Results

Figure 7A:
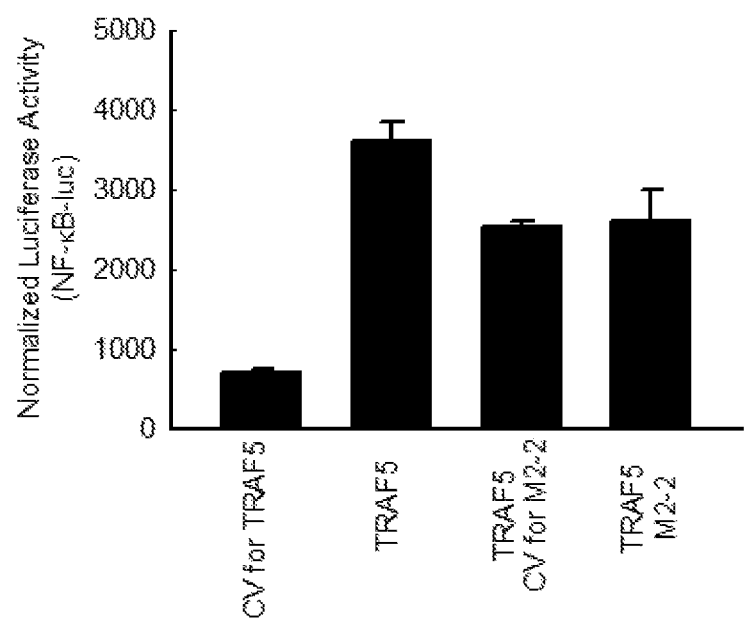
FIG. 7A-B contain data which illustrate that PDZ motifs 29-DEMI-32 and 39-KEALSDGI-46 of M2-2 protein suppress IRF-3 and NF-κB activation by inhibiting mitochondrial signalosome formation. In particular, Panel A shows the effect of M2-2 on TRAF-activated signaling. A549 cells were transfected a luciferase reporter plasmid NF-κB-Luc (0.5 μg/well), a plasmid encoding TRAF5 or its control (0.5 μg/well), and a plasmid encoding hMPV M2-2 or its mutants, or a control vector (0.1 μg/well). After 30 h, cells were harvested for luciferase activity measurement. Panel B shows the effect of motifs on the recruitment of TRAFs to mitochondrial compartment. A549 cells were infected with rhMPV-WT, rhMPV-E30M31, or rhMPV-E40L42D44, at MOI of 2, for 15 h and harvested to purify mitochondria. The abundance of mitochondria-associated MAVS, M2-2 and TRAF proteins was investigated by Western blot. Membranes were stripped and reprobed with anti-SDHA, as a control for comparable loading of samples. Data shown are representative of two independent experiments.

M2-2 did not block TRAF-5-induced signaling, confirming MAVS, but not its downstream signaling factors, as the target of M2-2 (FIG. 7A).

Example 8: The Effects of M2-2 PDZ Motifs on MAVS/TRAFs Signalosome

Materials and Methods

Antibodies: Monoclonal antibodies against Lamin b were obtained from Sigma-Aldrich (Sigma, St. Louis, Mo.). The polyclonal rabbit anti-hMPV antibodies were raised against purified hMPV by Creative Diagnostics, Shirley, N.Y. The polyclonal rabbit anti-MAVS antibody was a gift from Dr. Ilkka Julkunen (National Public Health Institute, Finland). The antibodies against TRAF2, TRAF3, and TRAF6 were from Cell Signaling, Danvers, Mass. FITC-conjugated goat anti-rabbit antibody was from Zymed, San Francisco, Calif. Primary antibodies against TRAF5 and horseradish-coupled secondary antibodies were purchased from Santa Cruz (Santa Cruz, Santa Cruz, Ca).

Cell line, growing conditions, infection: A549 cells were grown and infected, as in Example 2, with rhMPV-WT or M2-2 mutants at MOI of 2. Mock infection was used as a control. At 15 h p.i., mock-infected and infected A549 cells were harvested to prepare nuclear and cytosolic fractions, as in Example 6, and to prepare mitochondrial fractions.

Mitochondrial isolation: Mitochondria were isolated using the Qproteome Mitochondria Isolation Kit from Qiagen (Qiagen, Valencia, Calif.), according to manufacturer's instructions. Isolated mitochondria were resuspended in SDS sample buffer for Western blot analysis. The abundance of mitochondria-associated MAVS and TRAF proteins was investigated by Western blot, as in Example 3. Membranes were stripped and reprobed with anti-SDHA, as a control for comparable loading of samples. Purity of mitochondria was assessed by the mitochondrial marker SDHA, nuclear marker lamin-b, and by the absence of β-actin, a marker of cytoplasmic proteins.

Results

Figure 8:
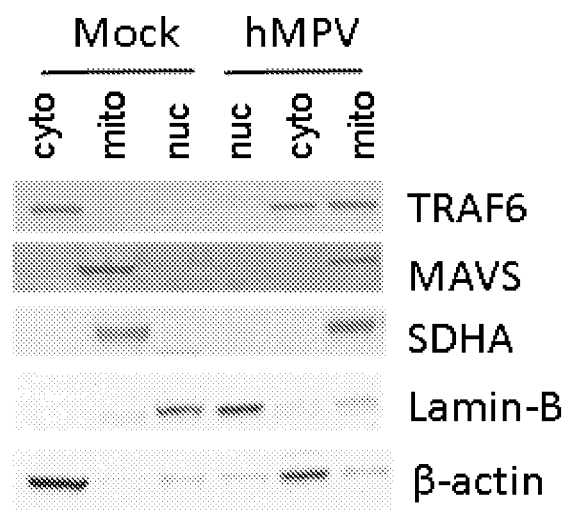
FIG. 8 contains data demonstrating the purity of isolated cellular compartments. A549 cells were infected with rhMPV-WT at MOI of 2. Mock infection was used as a control. At 15 h p.i., mitochondrial, cytosol and nuclear extracts were prepared. The abundance of mitochondria-associated MAVS and TRAF6 proteins was investigated by Western blot. The purity was demonstrated by the mitochondrial marker SDHA, nuclear marker lamin-b and cytosolic marker β-actin. Data shown are representative of two independent experiments.
Figure 9A:
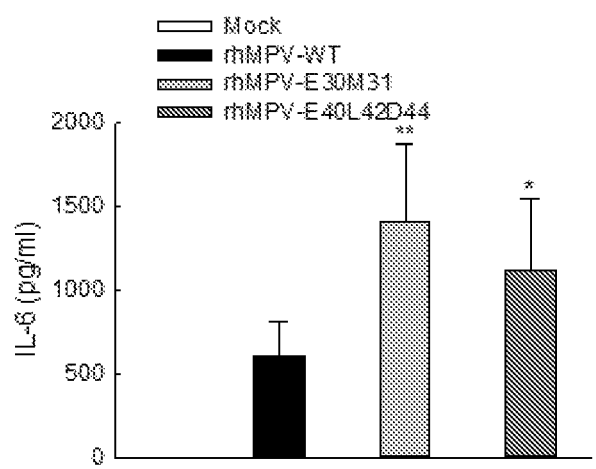
Figure 9B:
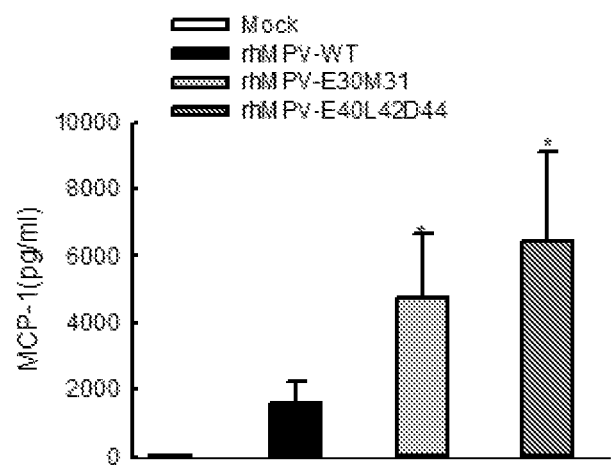
Figure 9E:
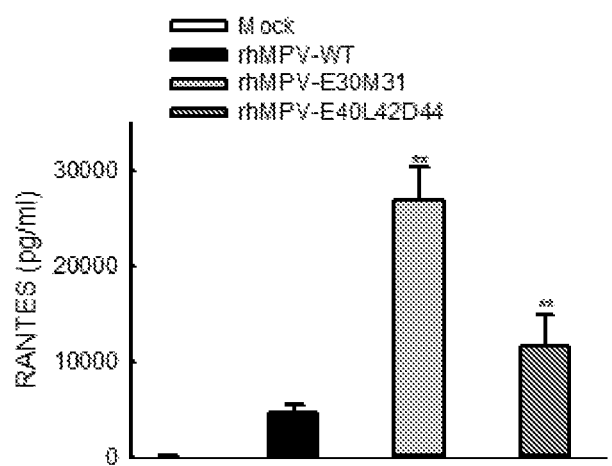
Figure 9F:
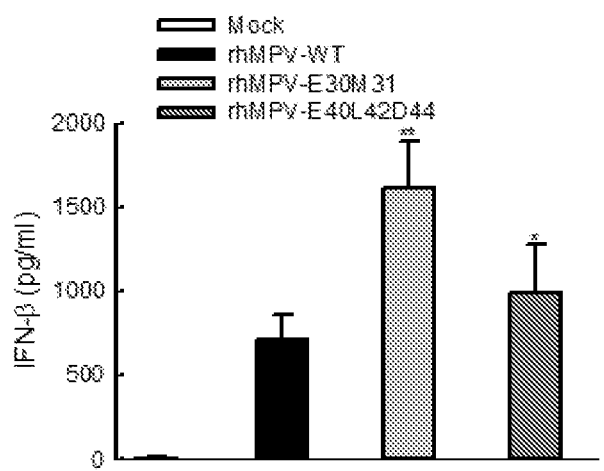
Figure 9I:
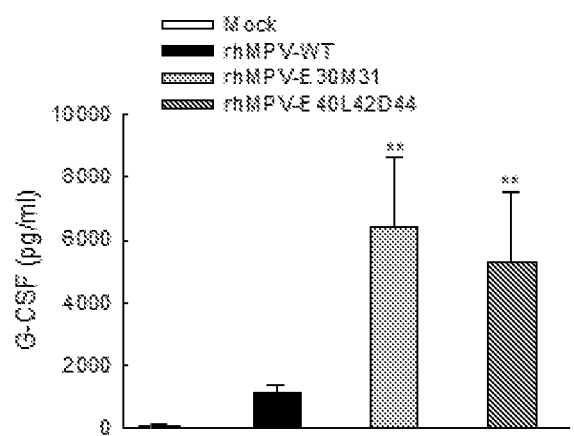
Figure 9J:
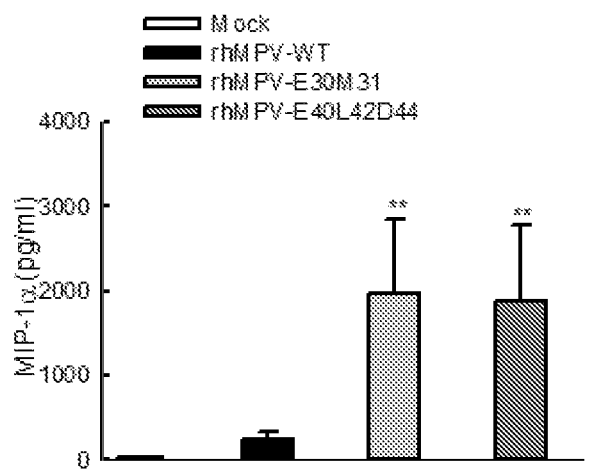

TRAF recruitment to mitochondria in response to rhMPV-WT and M2-2 mutants infection was investigated for TRAF 3, 5, and 6. In the isolated mitochondrial fractions, the mitochondrion purity was well controlled, as demonstrated by the expression of specific markers for cellular fractions during the preparation (FIG. 8).

Figure 7B:
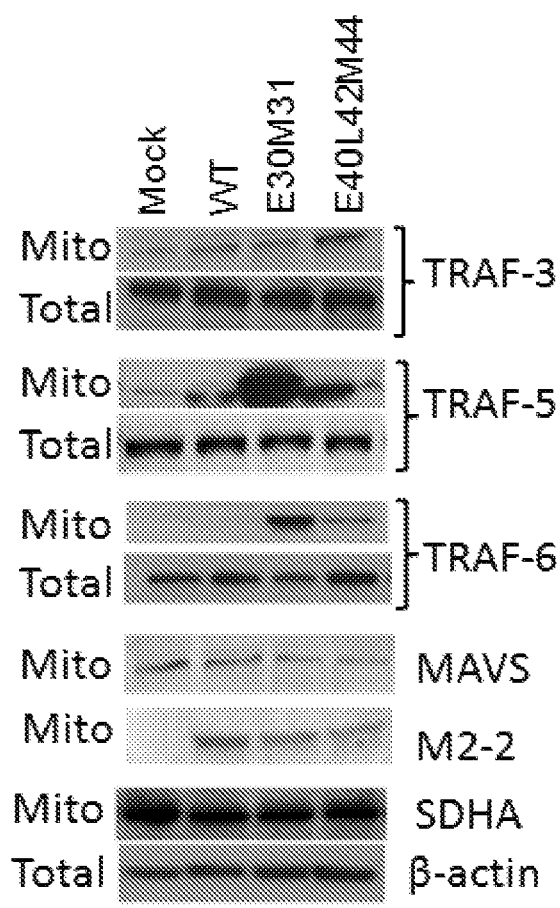

For TRAF3 recruitment to the mitochondria, rhMPV-E40L42D44-infected cells, but not rhMPV-E30M31-infected cells, had a slightly higher TRAF3 recruitment to mitochondria than WT-infected cells (FIG. 7B). For TRAF5, there was a significant increase in the abundance of mitochondria-associated TRAF5 in both rhMPV-E40L42D44- and rhMPV-E30M31-infected cells compared to WT-infected cells. The increase in TRAF5 recruitment was much less pronounced for rhMPV-E40L42D44-infected than for rhMPV-E30M31-infected cells. In terms of TRAF6 recruitment, both M2-2 mutants were able to recruit more TRAF6, with more recruitment in rhMPV-E30M31-infected cells than in rhMPV-E40L42D44-infected cells (FIG. 7B). To exclude the possibility that mutant-enhanced TRAF recruitment resulted from more MAVS in mitochondria, we investigated the abundance of MAVS and the mitochondrial protein SDHA (succinate dehydrogenase complex, subunit A, used as loading control). Slightly decreased MAVS in the mitochondria and stable levels of SDHA on exposure to mutant viruses suggest that this is not the case. In parallel to the slight decreased MAVS expression, mitochondrial M2-2 expression was also slightly declined in mutant-infected cells, suggesting that the binding of M2-2 protein to MAVS is maintained proportionally, even between WT- and mutant-infected cells. These results indicate the role of the PDZ motifs of M2-2 in inhibition of the MAVS-TRAF/3/5/6 interaction in infected cells.

One skilled in the art will readily appreciate that the present invention is adapted to carry out the objects and obtain the ends and advantages mentioned, as well as those inherent therein. The prior examples along with the methods, procedures, treatments, molecules, and specific compounds described herein are presently representative of preferred embodiments, are examples, and are not intended as limitations on the scope of the invention. Changes therein and other uses will occur to those skilled in the art which are encompassed within the spirit of the invention as defined by the scope of the claims.

The contents of the following references and all other references which are cited in this application are incorporated by reference in their entirety.

What is claimed is:

1. A live attenuated human metapneumovirus (hMPV) comprising a M2-2 protein that disrupts M2-2-mediated immune evasion, wherein the M2-2 protein has a PDZ-binding motif having an amino acid sequence of (i) SEQ ID NO:16 with amino acid substitutions corresponding to amino acids 2 and 3 of SEQ ID NO:16, or (ii) SEQ ID NO:17 with amino acid substitutions corresponding to amino acids 2, 4, and 6 of SEQ ID NO:17, or (iii) SEQ ID NO:16 with amino acid substitutions corresponding to amino acids 2 and 3 of SEQ ID NO:16 and SEQ ID NO:17 with amino acid substitutions corresponding to amino acids 2, 4, and 6 of SEQ ID NO:17.

2. A live attenuated human metapneumovirus (hMPV) comprising a M2-2 protein having PDZ-binding domain motif having an amino acid sequence of (i) SEQ ID NO:16 with amino acid substitution corresponding to amino acids 2 and 3 of SEQ ID NO:16 or (ii) SEQ ID NO:17 with amino acid substitution corresponding to amino acids 2, 4, and 6 of SEQ ID NO:17.

3. The human metapneumovirus (hMPV) of claim 2, wherein the expression of F protein and/or G protein is maintained.

4. An immunogenic composition comprising a live attenuated human metapneumovirus (hMPV) according to claim 1 and at least one of a pharmaceutically acceptable carrier, pharmaceutically acceptable excipient or an immune adjuvant.

5. The immunogenic composition of claim 4, which is suitable for intranasal, topical, parenteral, or enteral administration.

6. A method of eliciting an immune response in a subject in need thereof by administering a composition comprising a prophylactically or therapeutically effective amount of a live attenuated human metapneumovirus (hMPV) according to claim 1 or an immunogenic composition thereof.

7. The method of claim 6, wherein the subject is a human.

8. A method of treating or preventing human metapneumovirus (hMPV) infection in a subject by administering a therapeutically or prophylactically effective amount of a live attenuated human metapneumovirus (hMPV) according to claim 1 or an immunogenic composition thereof.

9. The method of claim 6, wherein the live attenuated human metapneumovirus (hMPV) or immunogenic composition thereof is intranasally administered.

10. The method of claim 9, wherein the live attenuated human metapneumovirus (hMPV) or immunogenic composition thereof is administered topically or systemically.

11. The method of claim 9, wherein the live attenuated human metapneumovirus (hMPV) or immunogenic composition is delivered using a mechanical liquid spray pump or an inhaler.

12. The live attenuated human metapneumovirus (hMPV) according to claim 1, wherein the live attenuated human metapneumovirus (hMPV) is formulated for intranasal delivery, for topical delivery, or systemic delivery.

13. A mechanical liquid spray pump or an inhaler comprising a live attenuated human metapneumovirus (hMPV) according to claim 1 or an immunogenic composition thereof.

14. The live attenuated human metapneumovirus (hMPV) of claim 1, wherein the M2-2 protein has the PDZ-binding motif of having the amino acid sequence of (i) SEQ ID NO:16 with amino acid substitutions corresponding to amino acids 2 and 3 of SEQ ID NO:16 or cii) the amino acid sequence of SEQ ID NO:17 with amino acid substitutions corresponding to amino acids 2, 4, and 6 of SEQ ID NO:17.

15. The method of claim 6, wherein the subject is an infant, a human child, elderly human, or immunocompromised human.

16. The method of claim 6, wherein the subject is equine, canine, feline, bovine, ovine, or avian.

17. A nucleic acid encoding the attenuated human metapneumovirus (hMPV) of claim 1.

18. A nucleic acid encoding the attenuated human metapneumovirus (hMPV) of claim 2.

19. The live attenuated human metapneumovirus (hMPV) of claim 1, wherein the amino acid substitutions are alanine substitutions.

20. The live attenuated human metapneumovirus (hMPV) of claim 2, wherein the amino acid substitutions are alanine substitutions.

* * * * *

SEQUENCE LISTING

<160> NUMBER OF SEQ ID NOS: 19

<210> SEQ ID NO 1
<211> LENGTH: 31
<212> TYPE: DNA
<213> ORGANISM: Artificial Sequence
<220> FEATURE:
<223> OTHER INFORMATION: PCR Primer

<400> SEQUENCE: 1
acgcgaaaaa aacgcgtata aattaagtta c                              31

<210> SEQ ID NO 2
<211> LENGTH: 41
<212> TYPE: DNA
<213> ORGANISM: Artificial Sequence
<220> FEATURE:
<223> OTHER INFORMATION: PCR Primer

<400> SEQUENCE: 2
tttgtcccgt tcttgattgc tagcattctt attctaactt g                   41

<210> SEQ ID NO 3
<211> LENGTH: 60
<212> TYPE: DNA
<213> ORGANISM: Artificial Sequence
<220> FEATURE:
<223> OTHER INFORMATION: PCR Primer

<400> SEQUENCE: 3
cgcgacgtct aatacgactc actataggga cgcgaaaaaa acgcgtataa attaagttac   60

<210> SEQ ID NO 4
<211> LENGTH: 25
<212> TYPE: DNA
<213> ORGANISM: Artificial Sequence
<220> FEATURE:
<223> OTHER INFORMATION: PCR Primer

<400> SEQUENCE: 4
gaatgctagc aatcaagaac gggac                                     25

<210> SEQ ID NO 5
<211> LENGTH: 30
<212> TYPE: DNA
<213> ORGANISM: Artificial Sequence
<220> FEATURE:
<223> OTHER INFORMATION: PCR Primer

<400> SEQUENCE: 5
tgttggtacc tacatgtttt actttagagc                                30

<210> SEQ ID NO 6
<211> LENGTH: 30
<212> TYPE: DNA
<213> ORGANISM: Artificial Sequence
<220> FEATURE:
<223> OTHER INFORMATION: PCR Primer

<400> SEQUENCE: 6
tgtaggtacc aacaatcaag aaaccaaaag                                30

<210> SEQ ID NO 7
<211> LENGTH: 62
<212> TYPE: DNA
<213> ORGANISM: Artificial Sequence
<220> FEATURE:
<223> OTHER INFORMATION: PCR Primer

<400> SEQUENCE: 7
ggtcggaccg cgaggaggtg gagatgccat gccgacccac ggcaaaaaaa ccgtatacat    60
tc                                                                  62

<210> SEQ ID NO 8
<211> LENGTH: 38
<212> TYPE: DNA
<213> ORGANISM: Artificial Sequence
<220> FEATURE:
<223> OTHER INFORMATION: PCR Primer

<400> SEQUENCE: 8
ctatagaggt tgatgcagcg atatggactc aaaaagaa                            38

<210> SEQ ID NO 9
<211> LENGTH: 50
<212> TYPE: DNA
<213> ORGANISM: Artificial Sequence
<220> FEATURE:
<223> OTHER INFORMATION: PCR Primer

<400> SEQUENCE: 9
caaaaagaat taaaagcagc tgcgtccgca gggatagtga agtcttcaca               50

<210> SEQ ID NO 10
<211> LENGTH: 41
<212> TYPE: DNA
<213> ORGANISM: Artificial Sequence
<220> FEATURE:
<223> OTHER INFORMATION: RT Primer

<400> SEQUENCE: 10
cgtctcagcc aatccctggt ttttttttt tctagttttg c                         41

<210> SEQ ID NO 11
<211> LENGTH: 20
<212> TYPE: DNA
<213> ORGANISM: Artificial Sequence
<220> FEATURE:
<223> OTHER INFORMATION: hMPV G Forward Primer

<400> SEQUENCE: 11
catcagtcca gtccgacagc                                                20

<210> SEQ ID NO 12
<211> LENGTH: 19
<212> TYPE: DNA
<213> ORGANISM: Artificial Sequence
<220> FEATURE:
<223> OTHER INFORMATION: hMPV Reverse Primer

<400> SEQUENCE: 12
cgtctcagcc aatccctgg                                                 19

<210> SEQ ID NO 13
<211> LENGTH: 49
<212> TYPE: DNA
<213> ORGANISM: Artificial Sequence
<220> FEATURE:
<223> OTHER INFORMATION: P Specific Primer

<400> SEQUENCE: 13

```
cgtctcagcc aatccctggt gattatgagt aattaaaaaa tgggacaag         49
```

<210> SEQ ID NO 14
<211> LENGTH: 19
<212> TYPE: DNA
<213> ORGANISM: Artificial Sequence
<220> FEATURE:
<223> OTHER INFORMATION: PCR Primer

<400> SEQUENCE: 14

```
cgtctcagcc aatccctgg                                          19
```

<210> SEQ ID NO 15
<211> LENGTH: 26
<212> TYPE: DNA
<213> ORGANISM: Artificial Sequence
<220> FEATURE:
<223> OTHER INFORMATION: PCR Primer

<400> SEQUENCE: 15

```
gcttcattac ccatgaaaag aatatc                                  26
```

<210> SEQ ID NO 16
<211> LENGTH: 4
<212> TYPE: PRT
<213> ORGANISM: Artificial Sequence
<220> FEATURE:
<223> OTHER INFORMATION: PDZ-binding motif

<400> SEQUENCE: 16

Asp Glu Met Ile
1

<210> SEQ ID NO 17
<211> LENGTH: 8
<212> TYPE: PRT
<213> ORGANISM: Artificial Sequence
<220> FEATURE:
<223> OTHER INFORMATION: PDZ-binding motif

<400> SEQUENCE: 17

Lys Glu Ala Leu Ser Asp Gly Ile
1               5

<210> SEQ ID NO 18
<211> LENGTH: 4
<212> TYPE: PRT
<213> ORGANISM: Artificial Sequence
<220> FEATURE:
<223> OTHER INFORMATION: PDZ-binding motif

<400> SEQUENCE: 18

Leu Glu Asn Ile
1

<210> SEQ ID NO 19
<211> LENGTH: 4
<212> TYPE: PRT
<213> ORGANISM: Artificial Sequence
<220> FEATURE:
<223> OTHER INFORMATION: PDZ-binding motif

<400> SEQUENCE: 19

Ile Glu Ile Ile
1